(12) United States Patent
Plettenburg et al.

(10) Patent No.: US 8,772,492 B2
(45) Date of Patent: Jul. 8, 2014

(54) SUBSTITUTED ISOQUINOLINE AND ISOQUINOLINONE DERIVATIVES

(75) Inventors: Oliver Plettenburg, Kelkheim (DE); Katrin Lorenz, Kelkheim (DE); Jochen Goerlitzer, Frankfurt am Main (DE); Matthias Lohn, Liederbach (DE)

(73) Assignee: Sanofi, Paris (FR)

(*) Notice: Subject to any disclaimer, the term of this patent is extended or adjusted under 35 U.S.C. 154(b) by 1286 days.

(21) Appl. No.: 12/487,409

(22) Filed: Jun. 18, 2009

(65) Prior Publication Data

US 2010/0056566 A1     Mar. 4, 2010

Related U.S. Application Data

(63) Continuation of application No. PCT/EP2007/011168, filed on Dec. 19, 2007.

(30) Foreign Application Priority Data

Dec. 27, 2006 (EP) .................................. 06026892

(51) Int. Cl.
| | | |
|---|---|---|
| A61K 31/47 | (2006.01) | |
| C07D 217/00 | (2006.01) | |
| C07D 401/12 | (2006.01) | |
| C07D 451/06 | (2006.01) | |
| C07D 405/14 | (2006.01) | |
| C07D 401/14 | (2006.01) | |

(52) U.S. Cl.
CPC ............ *C07D 401/12* (2013.01); *C07D 451/06* (2013.01); *C07D 405/14* (2013.01); *C07D 401/14* (2013.01)
USPC .......................................... 546/139; 514/307

(58) Field of Classification Search
None
See application file for complete search history.

(56) References Cited

U.S. PATENT DOCUMENTS

| | | | |
|---|---|---|---|
| 5,480,883 A | 1/1996 | Spada et al. | |
| 6,903,107 B1 | 6/2005 | Timmers et al. | |
| 7,217,722 B2 | 5/2007 | Takami et al. | |
| 7,618,985 B2 * | 11/2009 | Ray .............................. | 514/309 |
| 2003/0220368 A1 | 11/2003 | Ozaki et al. | |
| 2004/0138286 A1 | 7/2004 | Imazaki et al. | |
| 2006/0079556 A1 | 4/2006 | Sher et al. | |
| 2007/0060595 A1 | 3/2007 | Yoshizawa et al. | |
| 2008/0045566 A1 | 2/2008 | Ray et al. | |

FOREIGN PATENT DOCUMENTS

| | | |
|---|---|---|
| EP | 1403255 | 3/2004 |
| EP | 1541559 | 6/2005 |
| EP | 1550660 | 7/2005 |
| FR | 2485537 | 6/1980 |
| JP | 10087629 | 4/1998 |
| WO | 9202476 | 2/1992 |
| WO | 9706802 | 2/1997 |
| WO | 9723214 | 7/1997 |
| WO | WO 98/06433 | 2/1998 |
| WO | 9911642 | 3/1999 |
| WO | 0024718 | 5/2000 |
| WO | WO 0024718 A1 * | 5/2000 |
| WO | 0073299 | 12/2000 |
| WO | WO 01/39726 | 6/2001 |
| WO | 0153288 | 7/2001 |
| WO | 0156988 | 8/2001 |
| WO | 0164656 | 9/2001 |
| WO | WO 01/64238 | 9/2001 |
| WO | 0177101 | 10/2001 |
| WO | 0192227 | 12/2001 |
| WO | 0234712 | 5/2002 |
| WO | 02055496 | 7/2002 |
| WO | 02076457 | 10/2002 |
| WO | 02088101 | 11/2002 |
| WO | 03018556 | 3/2003 |
| WO | 03024450 | 3/2003 |
| WO | WO 03/053330 | 7/2003 |
| WO | 2004113297 | 12/2004 |
| WO | WO 2004/106325 | 12/2004 |
| WO | 2005035933 | 2/2005 |
| WO | 2005035516 | 4/2005 |
| WO | WO 2005/030130 | 4/2005 |
| WO | WO 2005/030791 | 4/2005 |
| WO | 2005054202 | 6/2005 |
| WO | 2005074535 | 8/2005 |
| WO | 2005087226 | 9/2005 |
| WO | 2005095362 | 10/2005 |

(Continued)

OTHER PUBLICATIONS

Alvarez, M. et al., "Product Class 5: Isoquinolines" Science of Synthesis (2005) pp. 661-838, vol. 15.

(Continued)

*Primary Examiner* — Heidi Reese
(74) *Attorney, Agent, or Firm* — Scully, Scott, Murphy & Presser, P.C.

(57) ABSTRACT

The invention relates to 6-substituted isoquinoline and isoquinoline derivatives of the formula (I)

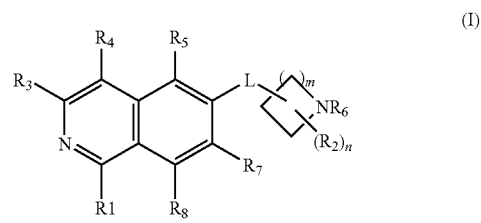

useful for the treatment and/or prevention of diseases associated with Rho-kinase and/or Rho-kinase mediated phosphorylation of myosin light chain phosphatase, and compositions containing such compounds.

48 Claims, No Drawings

(56) References Cited

FOREIGN PATENT DOCUMENTS

| WO | WO 2007/000240 | | 1/2007 |
|---|---|---|---|
| WO | 2007012421 | A1 | 2/2007 |
| WO | 2007012422 | A1 | 2/2007 |
| WO | 2007039563 | A1 | 4/2007 |
| WO | WO 2007/039563 | A1 | 4/2007 |
| WO | WO 2007/065916 | | 6/2007 |
| WO | 2008020081 | A1 | 2/2008 |
| WO | WO 2008/020081 | | 2/2008 |
| WO | 2008077555 | A2 | 7/2008 |
| WO | 2008077556 | A1 | 7/2008 |

OTHER PUBLICATIONS

Alvarez, M. et al., "Product Class 6: Isoquinolines" Science of Synthesis (2005) pp. 839-890, vol. 15.

Remington's Pharmaceutical Sciences 17th Edition (1985), p. 1418.

Forzato, C. et al., "Baker's yeast reduction of 4-hetero-2-(2-nitroethyl)cyclohexanones" Tetrahedron: Asymmetry (1997) pp. 1811-1820, vol. 8.

U.S. Appl. No. 12/970,376, filed Dec. 16, 2010, Inventor: Plettenburg, et al, entitled: "6-Substituted Isoquinolines and Isoquinolinones".

U.S. Appl. No. 13/000,754, filed Apr. 20, 2011, Inventor: Plettenburg et al., entitled: "Substituted Isoquinolines and Isoquinolinones as Rho Kinase Inhibitors".

U.S. Appl. No. 13/000,202, filed Dec. 20, 2010, Inventor: Plettenburg et al., entitled: "Bi- and Polycyclic Substituted Isoquinoline and Isoquinolinone Derivatives".

Bonjoch, J. et al., "A New Synthetic Entry to the Tricyclic Skeleton of FR901483 by Palladium-Catalyzed Cyclization of Vinyl Bromides with Ketone Enolates" Tetrahedron Letters (2003) pp. 8387-8390, vol. 44.

Iwakubo, M. et al., "Design and Synthesis of Rho Kinase Inhibitors (III)" Bioorganic & Medicinal Chemistry (2007) pp. 1022-1033, vol. 15.

Iwakubo, M. et al., "Design and Synthesis of Rho Kinase Inhibitors (II)" Bioorganic & Medicinal Chemistry (2007) pp. 350-364, vol. 15.

Tamura, M. et al., "Development of Specific Rho-Kinase Inhibitors and Their Clinical Application" Biochimica et Biophysica Acta (2005) pp. 245-252, vol. 1754.

Becker, D.P. et al., "A Short Synthesis of 1-Azaadamantan-4-one and the 4r and 4s Isomers of 4-Amino-1-azaadamantane" Synthesis (1992) pp. 1080-1082, vol. 11.

Degraffenreid, M.R. et al., "An Efficient and Scalable One-Pot Double Michael Addition-Dieckmann Condensation for the Synthesis of 4,4-Disubstituted Cyclohexane β-Keto Esters" Journal of Organic Chemistry (2007) pp. 7455-7458, vol. 72.

Lednicer, D. et al., "4-Amino-4-arylcyclohexanones and Their Derivatives, a Novel Class of Analgesics. 1. Modification of the Aryl Ring" Journal of Medicinal Chemistry (1980) pp. 424-430, vol. 23.

Caron, S. et al., "The Synthesis of a Selective PDE4/TNFα Inhibitor" Organic Process Research and Development (2001) pp. 587-592, vol. 5.

U.S. Appl. No. 11/961,193, filed Dec. 20, 2007, Plettenburg, et al.
U.S. Appl. No. 12/019,866, filed Jan. 25, 2008, Plettenburg, et al.
U.S. Appl. No. 12/019,799, filed Jan. 25, 2008, Plettenburg, et al.
U.S. Appl. No. 12/487,479, filed Jun. 18, 2009, Plettenburg, et al.
U.S. Appl. No. 12/487,455, filed Jun. 18, 2009, Plettenburg, et al.
U.S. Appl. No. 12/487,525, filed Jun. 18, 2009, Plettenburg, et al.
U.S. Appl. No. 12/487,386, filed Jun. 18, 2009, Plettenburg, et al.
U.S. Appl. No. 12/487,403, filed Jun. 18, 2009, Plettenburg, et al.
U.S. Appl. No. 12/487,503, filed Jun. 18, 2009, Plettenburg, et al.

Yoshii, A., et. al., Relaxation of Contracted Rabbit Tracheal and Human Bronchial Smooth Muscle by Y-27632 Through Inhibition of Ca2+ Sensitization, Am. J. Resp. Cell Mol. Biol., vol. 20, pp. 1190-1200, (1999).

Zhou, Y., et. al., Nonsteroidal Anti-Inflammatory Drugs Can Lower Amyloidogenic AB42 by Inhibiting Rho. Science, vol. 302, pp. 1215-1217, (2003).

Takami, et. al., Design and synthesis of rho kinase inhibitors, Bioorganic & Medicinal Chem. 2004 (12) 9 pp. 2115-2137.

Al, S., et. al., Rho-Rho Kinase Is Involved in Smooth Muscle Cell Migration Through Myosin Light Chain Phosphorylation—Dependent and Independent Pathways, Atherosclerosis, vol. 155, pp. 321-327, (2001).

Amano, M., et. al, Formation of Actin Stress Fibers and Focal Adhesions Enhanced by Rho-Kinase, Science, vol. 275, pp. 1308-1311, (1997).

Bauer, M., et. al, Dichotomous Regulation of Myosin Phosphorylation and Shape Change by Rho-Kinase and Calcium in Intact Human Platelets, Blood, vol. 94, No. 5, (1999), pp. 1665-1672.

Chellaiah, M., et. al.,, Rho-Dependent Rho Kinase Activation Increases CD44 Surface Expression and Bone Resorption in Osteoclasts, The Journal of Biological Chemistry. vol. 278, No. 31, (2003), pp. 29086-29097.

Chitaley, K., et. al., Antagonism of Rho-Kinase Stimualates Rat Penlle Erection via a Nitric Ovide-Independent Pathway, Nature Medicine, vol. 7, No. 1, (2001), pp. 119-122.

Demiryurek, S., et. al., Effects of Fasudil, a Rho-Kinase Inhibitor, On Myocardial Preconditioning in Anesthetized Rats, European Journal of Pharmacology, vol. 527, (2005), pp. 129-140.

Fukumoto, Y., et. al., Acute Vasodilator Effects of a Rho-Kinase Inhibitor, Fasudil, in Pateients With Severe Pulmonary Hypertension, Heart, (2005), vol. 91, pp. 391-392.

Furukawa, N., et. al., Role of Rho-Kinase in Regulation of Insulin Action and Glucose Homeostasis, Cell Metabolism, vol. 2, pp. 119-129, (2005).

Gingras, D., et. al., Tyrosine Phosphorylation of the Vascular Endothelial-Growth-Factor Receptor-2 (VEGFR-2) is Modulated by Rho Proteins, Biochem. J., (2000), vol. 348, pp. 273-280.

Gokina, N. I., et. al., Effects of Rho Kinase Inhibition on Cerebral Artery Myogenic Tone and Reactivity, J. Appl. Physiol. vol. 98, pp. 1940-1948, (2005).

Hara, M., et. al., Protein Kinase Inhibition by Fasudil Hydrochloride Promotes Neurological Recovery After Spinal Cord Injury in Rats, J Neurosurg. (Spine 1), vol. 93, pp. 94-101, (2000).

Hattori, T., et. al., Long-Term Inhibition of Rho-Kinase Suppresses Left Ventricular Remodeling After Myocardial Infarction in Mice, Circulation, (2004), vol. 109, pp. 2234-2239.

Okada, H., et. al., Synthesis and Antitumor Activities of Prodrugs of Benzoylphenylureas, Chem. Pharm. Bull (1994), pp. 57-61, vol. 42, No. 1.

Hitomi, A., et. al., Hemorheological Abnormalities in Experimental Cerebral Ischemia and Effects of Protein Kinase Inhibitor on Blood Fluidity, Life Sciences, vol. 67, (2000), pp. 1929-1939.

Honjo, M., et. al., Effects of Rho-Associated Protein Kinase Inhibitors Y-27632 on Intraocular Pressure and Outflow Facitlity, Investigative Ophthalmology & Visual Science, (2001), vol. 42, No. 1, pp. 137-144.

Inoue, M., et. al., Initiation of Neuropathic Pain Requires Lysophospatidic Acid Receptor Signaling, Nature Medicine, vol. 10, No. 7, pp. 712-718, (2004).

Itoh, et. al., An Essential Part for Rho-Associated Kinase in the Transcellular Invasion of Tumor Cells, Nature Medicine, vol. 5, No. 2, pp. 221-225, (1999).

Kawaguchi, A., et. al., The Effect of a Rho Kinase Inhibitor Y-27632 on Superoxide Production, Aggregation and Adhesion in Human Polymorphonuclear Leukocytes, European Journal of Pharmacology, vol. 403, (2000), pp. 203-208.

Kim, I., et. al., Thin and Thick Filament Regulation of Contractility in Experimental Cerebral Vasospasm, Neurosurgery, vol. 46, No. 2, (2000), pp. 440-447.

Kimura, K., et. al., Regulation of the Association of Adducin With Actin Filaments by Rho-Associated Kinase (Rho-Kinase) and Myosin Phosphatase, The Journal of Biological Chemistry, vol. 273, No. 10, pp. 5542-5548, (1998).

Kishi, T., et. al., Rho-Kinase Inhibitor Improves Increased Vascular Resistance and Impaired Vasodilation of the Forearm in Patients With Heart Failure, Circulation, (2005), vol. 111, pp. 2741-2747.

(56) References Cited

OTHER PUBLICATIONS

Klages, B., et. al., Activation of G12/G13 Results in Shape Change and Rho/Rho-Kinase-Mediated Myosin Light Chain Phosphorylation in Mouse Platelets, The Journal of Cell Biology, vol. 144, No. 4, (1999), pp. 745-754.

Lin, T., et al., Rho-ROCk-LIMK-Cofilin Pathway Regulates Shear Stress Activation of Sterol Regulatory Element Binding Proteins, Circulation Research, (2003), vol. 92, pp. 1296-1304.

Maruoka, S., et. al., Elastase Anti-Elastase Imbalance in the Pathogenesis of COPD, Nippon Rinsho, (1999), vol. 57, pp. 1982-1987.

Masumoto, A. et. al., Suppression of Coronary Artery Spasm by the Rho Kinase Inhibitor Fasudil in Patients With Vasospastic Angina, Circulation, (2002), vol. 105, pp. 1545-1547.

Nakahara, T., et. al., Y-27632 Potentiates Relaxant Effects of B2-Adrenoceptor Agonists in Bovine Tracheal Smooth Muscle, European Journal of Pharmacology, vol. 389, (2000), pp. 103-106.

Negoro, N., et. al., The Kinase Inhibitor Fasudil (HA-1077) Reduces Intimal Hyperplasia through Inhibiting Migration and Enhancing Cell Loss of Vascular Smooth Muscle Cells, Biochemical and Biophysical Research Communications, vol. 262, pp. 211-215, (1999).

Noma, K., et. al., Physiological Role of ROCKS in the Cardiovascular System, Am. J. Physiol. Cell Physiol., vol. 290, pp. C661-C668, (2006).

Pacaud, P., et. al., Rho Proteins and Vascular Diseases, Archives Des Maladies Du CCeur Et Des Vaisseaux, vol. 98, pp. 249-254, (2005).

Pommereau, A., et. al., Two Simple and Generic Antibody-Independent Kinase Assays: Comparison of a Bioluminescent and a Microfluidic Assay Format, J. Biomol. Screen, (2004), vol. 9, pp. 409-416.

Retzer, M., et. al., Lysophosphatidic Acid-Induced Platelet Shape Change Proceeds Via Rho/Rho Kinase-Mediated Myosin Light-Chain and Moesin Phosphorylation, Cellular Signalling, vol. 12. pp. 645-648, (2000).

Retzer, M., et. al., Mildly Oxidised Low Density Lipoprotein Induces Platelet Shape Change Via Rho-Kinase-Dependent Phosphorylation of Myosin Light Chain and Moesin, FEBS Letters, vol. 466, pp. 70-74, (2000).

Sandu, O. A., et. al., Diabetes in the Goto-Kakizaki Rat Is Accompanied by Impaired Insulin-Mediated Myosin-Bound Phosphatase Activation and Vascular Smooth Muscle Cell Relaxation, Diabetes, vol. 49, (2000), pp. 2178-2189.

Sato, M., et. al., Involvement of Rho-Kinase-Mediated Phosphorylation of Myosin Light Chain in Enhancement of Cereberal Vasospasm, Circulation Research, (2000), vol. 87, pp. 195-200.

Satoh, S.-I., et. al., Pharmacological Profile of Hydroxy Fasudil as a Selective Rho Kinase Inhitor on Ischemic Brain Damage, Life Sciences, vol. 69, (2001), pp. 1441-1453.

Seasholtz, T. M., et. al., Rho and Rho Kinase Mediate Thrombin-Stimulated Vascular Smooth Muscle Cell DNA Synthesis and Migration , Circulation Research, (1999), vol. 84, pp. 1186-1193.

Setoguchi, H., et al., Leukotriene C4 Enhances the Contraction of Porcine Tracheal Smooth Muscle Through the Activation of Y-27632, a Rho Kinase Inhibitor, Sensitive Pathway, British Journal of Pharmacology, (2001), vol. 132, pp. 111-118.

Shimokawa, H., et al., Anti-Anginal Effect of Fasudil, a Rho-Kinase Inhibitor, in Patients With Stable Effort Angina: A Multicenter Study, Journal of Cardiovascular Pharmacology, (2002), vol. 40, pp. 751-761.

Somlyo, A. V., et. al., Rho-Kinase Inhibitor Retards Migration and In Vivo Dissemination of Human Prostate Cancer Cells, Biochemical and Biophysical Research Communications, vol. 269, pp. 652-659, (2000).

Steioff, K., et. al., Long Term Rho-Kinase Inhibition Ameliorates Endothelial Dysfunction in LDL-Receptor Deficient Mice, European Journal of Pharmacology, vol. 512, (2005), pp. 247-249.

Tatsumi, S., et. al., Involvement of Rho-Kinase in Inflammatory and Neuropathic Pain Through Phosphorylation of Myristoylated Alainine-Rich C-Kinase Substrate (MARCKS), Neuroscience, vol. 131, pp. 491-498, (2005).

Totsukawa, G., et. al., Distinct Roles of ROCK (Rho-Kinase) and MLCK in Spatial Regulation of MLC Phosphorylation for Assembly of Stress Fibers and Focal Adhesions in 3T3 Fibroblasts, The Journal of Cell Biology, vol. 150, No. 4, pp. 797-806, (2000).

Uchida, S., et. al., The Suppression of Small GTPase Rho Signal Transduction Pathway Inhibits Angiogenesis in Vitro and in Vivo, Biochemical and Biophysical Research Communications, vol. 269, pp. 633-640, (2000).

Uehata, M., et al., Calcium Sensitization of Smooth Muscle Mediated by a Rho-Associated Protein Kinase in Hypertension, Nature, vol. 389, pp. 990-994, (1997).

Vicente-Manzanares, M., et. al., A Role for the Rho-p160 Rho Coiled-Coil Kinase Axis in the Chemokine Stromal Cell-Derived Factor-1a-Induced Lymphocyte Actomyosin and Microtubular Organization and Chemotaxis, The Journal of Immunology, (2002), vol. 168, pp. 400-410.

Vicente-Manzanares, M., et. al., The RhoA Effector MDia Is Induced During T Cell Activation and Regulates Actin Polymerization and Cell Migration in T Lymphocytes, The Journal of Immunology, (2003), vol. 171, pp. 1023-1034.

Wakino, S., et. al., Rho/Rho Kinase as a Potential Target for the Treatment of Renal Disease, Drug News Perspective, (2005), vol. 18, pp. 639-643.

Yamakawa, T., et. al., Involvement of Rho-Kinase in Angiotensin II—Induced Hypertrophy of Rat Vascular Smooth Muscle Cells, Hypertension, (2000), vol. 35, pp. 313-318.

Yamamoto, Y., et al., The Protein Kinase Inhibitor Fasudil Protects Against Ischemic Myocardial Injury Induced by Endothelin-1 in the Rabbit, Journal of Cardiovascular Pharmacology, vol. 35, pp. 203-211, (2000).

Yoshida, Y., et. al., Studies on Anti-Helicobacter pylori Agents. Part 1: Benzyloxyisoquinoline Derivatives, Bioorg. & Med. Chem., vol. 7 (1999), pp. 2647-2666.

Curran, T.T., et al., "The Preparation of Optically Active 2-Cyclopentan-1,4-Diol Derivatives from Furfurl Alcohol", Tetrahedron, pp. 1983-2004, vol. 53(6), Feb. 10, 1997.

\* cited by examiner

SUBSTITUTED ISOQUINOLINE AND ISOQUINOLINONE DERIVATIVES

FIELD OF THE INVENTION

The present invention relates to novel isoquinoline and isoquinolinone derivatives as described in the claims, their preparation and their use in the treatment and/or prevention of diseases related to the inhibition of Rho-kinase and/or of Rho-kinase mediated phosphorylation of myosin light chain phosphatase.

BACKGROUND OF THE INVENTION

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al., Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-8), bronchial smooth muscle contraction (Yoshii et al. Am. J. Resp. Cell Mol. Biol. 20, 1190-1200), asthma (Setoguchi et al. Br J. Pharmacol. 2001, 132, 111-8; Nakahara, et al. Eur J 2000, 389, 103) and chronic obstructive pulmonary disease (COPD, Maruoka, Nippon Rinsho, 1999, 57, 1982-7), hypertension, pulmonary hypertension (Fukumoto et al. Heart, 91, 391-2, 2005, Mukai et al. Nature 1997, 389, 990-4) and ocular hypertension and regulation of intraoccular pressure (Honjo et al. Invest. Opthalmol. Visual Sci. 2001, 42, 137-144), endothelial dysfunction (Steioff et al. Eur. J. Pharmacol. 2005, 512, 247-249), angina (Masumoto et al. Circ 2002, 105, 1545-47, Shimokawa et al. JCP, 2002, 40, 751-761), nephropathy, including hypertension-induced, non-hypertension-induced, and diabetic nephropathies, renal failure and peripheral arterial occlusive disease (PAOD) (Wakino et al. Drug News Perspect. 2005, 18, 639-43), myocardial infarction (Demiryurek et al. Eur J Pharmacol. 2005, 527, 129-40, Hattori et al. Circulation, 2004, 109, 2234-9), cardiac hypertrophy and failure (Yamakawa, et al. Hypertension 2000, 35, 313-318, Liao et al. Am J Physiol Cell Physiol. 2006, 290, C661-8, Kishi et al. Circ 2005, 111, 2741-2747), coronary heart disease, artherosclerosis, restenosis (Pacaud et al. Arch. Mal. Coeur 2005, 98, 249-254, Retzer, et al. FEBS Lett 2000, 466, 70, Negoro, et al. Biochem Biophys Res Commun 1999, 262, 211), diabetes, diabetic complications, glucose utilization and metabolic syndrome (Sandu, et al. Diabetes 2000, 49, 2178, Maeda et al. Cell Metab. 2005, 2, 119-29), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Hara, et al. J Neurosurg 2000, 93, 94), cerebral ischemia (Uehata, et al. Nature 1997, 389, 990; Satoh et al. Life Sci. 2001, 69, 1441-53; Hitomi, et al. Life Sci 2000, 67, 1929; Yamamoto, et al. J Cardiovasc Pharmacol. 2000, 35, 203-11), cerebral vasospasm (Sato, et al. Circ Res 2000, 87, 195; Kim, et al. Neurosurgery 2000, 46, 440), pain, e.g. neuropathic pain (Tatsumi, et al. Neuroscience 2005, 131, 491, Inoue, et al. Nature medicine 2004, 10, 712), infection of digestive tracts with bacteria (WO 98/06433), cancer development and progression, neoplasia where inhibition of Rho kinase has been shown to inhibit tumor cell growth and metastasis (Itoh, et al. Nature Medicine 1999, 5, 221; Somlyo, et al. Res Commun 2000, 269, 652), angiogenesis (Uchida, et al. Biochem Biophys Res 2000, 269, 633-40; Gingras, et al. Biochem J 2000, 348, 273), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa, et al. FEBS Lett. 2000, 466, 70-74; Bauer et al. Blood 1999, 94, 1665-1672, Klages, et al. J Cell Biol 1999, 144, 745; Retzer, et al. Cell Signal 2000, 12, 645) and leukocyte aggregation (Kawaguchi, et al. Eur J Pharmacol. 2000, 403:203-8; Sanchez-Madrid, et al. J Immunol. 2003, 171, 1023-34, Sanchez-Madrid, et al. J Immunol. 2002, 168, 400-10), and bone resorption (Chellaiah, et al. J Biol Chem. 2003, 278, 29086-97). Na/H exchange transport system activation (Kawaguchi, et al. Eur J Pharmacol. 2000, 403: 203-8), Alzheimer's disease (Zhou et al. Science 2003, 302, 1215-1217), adducin activation (Fukata et al. J. Biol. Chem., 1998, 273, 5542-5548), and in SREB (Sterol response binding element) signalling and its effects on lipid metabolism (Lin et al. Circ. Res., 92, 1296-304, 2003).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

WO 01/64238 describes isoquinoline-5-sulfonamide derivatives optionally substituted by a —$(CH_2)_{1-6}$—O—$(CH_2)_{0-6}$—, a —$(CH_2)_{0-6}$—S—$(CH_2)_{0-6}$— or a —$(CH_2)_{0-6}$-linked heterocyclic group useful as neuroprotective agents.

WO 2004/106325 (Schering A G) describes prodrugs of the Rho-kinase inhibitor fasudil carrying an ether or ester group in the 1-position of the isoquinoline ring.

WO 2001/039726 generically describes —O—$(C_0-C_{10})$ alkyl-heteroaryl substituted cyclohexyl derivatives useful for the treatment of microbial infections.

JP 10087629 A describes isoquinoline derivatives useful for the treatment of diseases caused by *Heliobacter pylori* such as for example gastritis cancer or ulcer. The isoquinoline derivatives may be substituted by OH in the 1-position and are preferably 5-substituted by X—[$(C_1-C_6)$alkylene)]$_{0-1}$—Y wherein X may be oxygen and Y may be an aryl or a heterocyclic group.

Hagihara et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I-X—Ar II" wherein X may be $(CHR_1)_m$—Z—$(CHR_1)_n$, e.g. Z—$CH_2$, wherein Z may be O, $R_1$ is hydrogen or alkyl, Ar I may be among others an optionally substituted isoquinolone and Ar II may be among others an optionally substituted $C_{3-7}$ monocyclic saturated heterocyclic system.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group $(CR^eR^f)_pOR^{43}$ wherein p may be zero, and $R^{43}$ is e.g. a $(C_3-C_{10})$cycloalkyl residue optionally substituted by $NR^{51}R^{52}$, wherein $R^{51}$ and $R^{52}$ may be hydrogen, $(C_1-C_6)$ alkyl etc.; or $R^{43}$ is a group $R^{81}$ defined as a 4-6 membered unsaturated or saturated monocyclic heterocylic ring with 1, 2, 3 or 4 heteroatoms; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxyl in the 1-position and are optionally substituted in 6-position by a group $(CR^eR^f)_pOR^{43}$ wherein p may be zero, and $R^{43}$ is e.g. a $(C_3-C_{10})$cycloalkyl residue optionally substituted by $NR^{51}R^{52}$, wherein $R^{51}$ and $R^{52}$ may be hydrogen, $(C_1-C_6)$alkyl etc.; or $R^{43}$ is a group $R^{81}$ defined as a 4-6 membered unsaturated or saturated monocyclic heterocyclic ring with 1, 2, 3 or 4 heteroatoms; and are substituted by a directly bound optionally substituted aryl or heteroaryl ring in the 4-position.

WO 03/053330 (Ube) generically describes isoquinolone derivatives of the formula

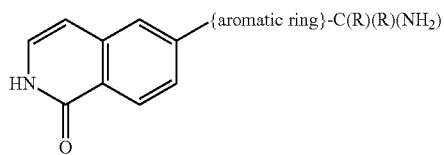

as Rho-kinase inhibitors.

SUMMARY OF THE INVENTION

An embodiment of the present invention is a compound of the formula (I)

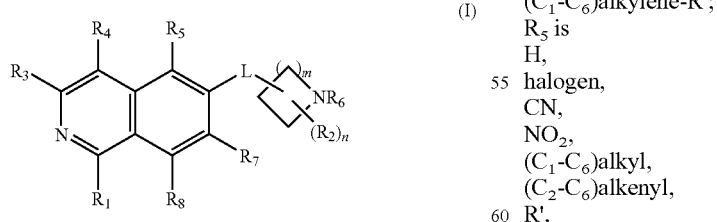

wherein
$R_1$ is H, OH or $NH_2$;
$R_2$ is
R',
$(C_7-C_8)$alkyl,
$(C_1-C_6)$alkylene-R',
$(C_2-C_6)$alkenyl,
$(C_2-C_6)$alkynyl,
$(C_1-C_6)$alkylene-O—$(C_1-C_6)$alkyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)$NH_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
C(O)O—$(C_1-C_6)$alkyl,
C(O)OR'
C(O)$(C_1-C_6)$alkyl,
C(O)R',
C(O)NH—$(C_1-C_6)$alkyl,
C(O)NHR',
C(O)—NH$(C_2-C_6)$alkenyl,
C(O)—NH$(C_2-C_6)$alkynyl,
C(O)—NH$(C_1-C_6)$alkylene-R',
C(O)N[$(C_1-C_6)$alkyl]R'
C(O)N[$(C_1-C_6)$alkyl]$_2$,
C(O)—$(C_1-C_6)$alkylene-R',
C(O)O$(C_1-C_6)$alkylene-R'; or
$R_2$ is $(C_1-C_6)$alkyl, provided that in said alkyl residue at least one hydrogen is substituted by OH, $OCH_3$, COOH, $COOCH_3$, $NH_2$, $NHCH_3$, $N(CH_3)_2$, $CONH_2$, $CONHCH_3$ or $CON(CH_3)_2$; or
$R_2$ is a $(C_1-C_4)$alkylene bound to the cyclic amine, in which the $(C_1-C_4)$alkylene forms a second bond to a different carbon atom of the cyclic amine ring and forms, together with carbon atoms of cyclic amine, a second, 4-8 membered ring;
$R_3$ is
H,
halogen,
$(C_1-C_6)$alkyl,
$(C_1-C_6)$alkylene-R',
OH,
O—R",
$NH_2$,
NHR",
NR"R" or
NH—C(O)—R",
$R_4$ is
H,
halogen,
hydroxy,
CN,
$(C_1-C_6)$alkyl,
R',
$(C_1-C_6)$alkylene-R';
$R_5$ is
H,
halogen,
CN,
$NO_2$,
$(C_1-C_6)$alkyl,
$(C_2-C_6)$alkenyl,
R',
$(C_1-C_6)$alkylene-$(C_6-C_{10})$aryl,
$(C_2-C_6)$alkenylene-$(C_6-C_{10})$aryl,
$(C_1-C_6)$alkylene-$(C_5-C_{10})$heterocyclyl,
CH(OH)—$(C_1-C_6)$alkyl,
$NH_2$,
NH—R',
NH—$SO_2$H, NH—SO$_2$—(C$_1$-C$_6$)alkyl,
NH—SO$_2$—R',
NH—C(O)—(C$_1$-C$_6$)alkyl,
NH—C(O)—R',
C(O)N[(C$_1$-C$_6$)alkyl]$_2$,
C(O)OH, or
C(O)O—(C$_1$-C$_6$)alkyl;
R$_6$ is
H,
R',
(C$_1$-C$_8$)alkyl,
(C$_1$-C$_6$)alkylene-R',
(C$_1$-C$_6$)alkylene-O—(C$_1$-C$_6$)alkyl,
(C$_1$-C$_6$)alkylene-O—R',
(C$_1$-C$_6$)alkylene-CH[R']$_2$,
(C$_1$-C$_6$)alkylene-C(O)—R',
(C$_1$-C$_6$)alkylene-C(O)NH$_2$,
(C$_1$-C$_6$)alkylene-C(O)NH—R',
(C$_1$-C$_6$)alkylene-C(O)NH—(C$_1$-C$_6$)alkyl,
(C$_1$-C$_6$)alkylene-C(O)N[(C$_1$-C$_6$)alkyl]$_2$,
(C$_1$-C$_6$)alkylene-C(O)N[R']$_2$;
(C$_1$-C$_6$)alkylene-C(O)O—(C$_1$-C$_6$)alkyl,
C(O)O—(C$_1$-C$_6$)alkyl,
C(O)OR'
C(O)(C$_1$-C$_6$)alkyl,
C(O)R',
C(O)NH—(C$_1$-C$_6$)alkyl,
C(O)NHR',
C(O)N[(C$_1$-C$_6$)alkyl]R'
C(O)N[(C$_1$-C$_6$)alkyl]$_2$,
C(O)—(C$_1$-C$_6$)alkylene-R', or
C(O)O(C$_1$-C$_6$)alkylene-R';
R$_7$ is
H,
halogen,
CN,
NO$_2$,
(C$_1$-C$_6$)alkyl,
O—(C$_1$-C$_6$)alkyl,
(C$_2$-C$_6$)alkenyl,
R',
(C$_2$-C$_6$)alkenylene-(C$_6$-C$_{10}$)aryl,
(C$_1$-C$_6$)alkylene-R',
CH(OH)—(C$_1$-C$_6$)alkyl,
NH$_2$,
NH—R',
NH—SO$_2$H,
NH—SO$_2$—(C$_1$-C$_6$)alkyl,
NH—SO$_2$—R',
SO$_2$—NH$_2$,
SO$_2$—NHR',
NH—C(O)—(C$_1$-C$_6$)alkyl,
NH—C(O)—R',
C(O)N[(C$_1$-C$_6$)alkyl]$_2$,
C(O)OH, or
C(O)O—(C$_1$-C$_6$)alkyl;
R$_8$ is H, halogen or (C$_1$-C$_6$)alkyl;
n is 1, 2, 3 or 4;
m is 1, 2, 3, 4 or 5; and
L is O—(CH$_2$)p, S(CH$_2$)p, S(O)(CH$_2$)p, SO$_2$(CH$_2$)p, NH(CH$_2$)p, N(C$_1$-C$_6$)alkyl-(CH$_2$)p, N(C$_3$-C$_6$)cycloalkyl-(CH$_2$)p, N[CO(C$_1$-C$_6$)alkyl]-(CH$_2$)p or N[(C$_1$-C$_3$)alkylene-R']-(CH$_2$)p;
p is 0, 1, 2, 3, or 4;
R' is
(C$_3$-C$_8$)cycloalkyl,
(C$_5$-C$_{10}$)heterocyclyl,
(C$_6$-C$_{10}$)aryl; and
R" is
(C$_3$-C$_8$)cycloalkyl,
(C$_5$-C$_{10}$)heterocyclyl,
(C$_6$-C$_{10}$)aryl,
(C$_1$-C$_6$)alkyl,
(C$_1$-C$_6$)alkylene-R',
(C$_1$-C$_6$)alkylene-O—(C$_1$-C$_6$)alkyl,
(C$_1$-C$_6$)alkylene-O—R', or
(C$_1$-C$_6$)alkylene-NR$_x$R$_y$; and
R$_x$ and R$_y$ are independently of each other
(C$_1$-C$_6$)alkyl,
(C$_5$-C$_{10}$)heterocyclyl,
(C$_6$-C$_{10}$)aryl,
(C$_1$-C$_4$)alkylene-(C$_5$-C$_{10}$)heterocyclyl,
(C$_1$-C$_4$)alkylene-(C$_6$-C$_{10}$)aryl,
(C$_1$-C$_4$)alkylene-NH(C$_1$-C$_6$)alkyl,
(C$_1$-C$_4$)alkylene-N[(C$_1$-C$_6$)alkyl]$_2$,
(C$_1$-C$_4$)alkylene-N[(C$_6$-C$_{10}$)aryl]$_2$, or
(C$_1$-C$_4$)alkylene-N[(C$_5$-C$_{10}$)heterocyclyl]$_2$;
wherein in residues R$_4$, R$_5$, R$_6$, R$_7$ and R$_8$ as alkyl, alkylene or cycloalkyl can optionally be substituted one or more times by OH, OCH$_3$, COOH, COOCH$_3$, NH$_2$, NHCH$_3$; N(CH$_3$)$_2$, CONH$_2$, CONHCH$_3$ or CON(CH$_3$)$_2$;
wherein in residues R$_2$ to R$_8$ as alkyl or alkylene can optionally be substituted one or more times by halogen;
wherein in residues R$_2$ to R$_8$ as (C$_6$-C$_{10}$)aryl and (C$_5$-C$_{10}$)heterocyclyl are unsubstituted or substituted one or more times by suitable groups independently selected from halogen, OH, NO$_2$, N$_3$, CN, C(O)—(C$_1$-C$_6$)alkyl, C(O)—(C$_6$-C$_{10}$)aryl, COOH, COO(C$_1$-C$_6$)alkyl, CONH$_2$, CONH(C$_1$-C$_6$)alkyl, CON[(C$_1$-C$_6$)alkyl]$_2$, (C$_3$-C$_8$)cycloalkyl, (C$_1$-C$_6$)alkyl, (C$_1$-C$_6$)alkylene-OH, (C$_1$-C$_6$)alkylene-NH$_2$, (C$_1$-C$_6$)alkylene-NH(C$_1$-C$_6$)alkyl, (C$_1$-C$_6$)alkylene-N[(C$_1$-C$_6$)alkyl]$_2$, (C$_2$-C$_6$)alkenyl, (C$_2$-C$_6$)alkynyl, O—(C$_1$-C$_6$)alkyl, O—C(O)—(C$_1$-C$_6$)alkyl, PO$_3$H$_2$, SO$_3$H, SO$_2$—NH$_2$, SO$_2$NH(C$_1$-C$_6$)alkyl, SO$_2$N[(C$_1$-C$_6$)alkyl]$_2$, S—(C$_1$-C$_6$)alkyl, SO—(C$_1$-C$_6$)alkyl, SO$_2$—(C$_1$-C$_6$)alkyl, SO$_2$—N═CH—N[(C$_1$-C$_6$)alkyl]$_2$, C(NH)(NH$_2$), NH$_2$, NH—(C$_1$-C$_6$)alkyl, N[(C$_1$-C$_6$)alkyl]$_2$, NH—C(O)—(C$_1$-C$_6$)alkyl, NH—C(O)O—(C$_1$-C$_6$)alkyl, NH—SO$_2$—(C$_1$-C$_6$)alkyl, NH—SO$_2$—(C$_6$-C$_{10}$)aryl, NH—SO$_2$—(C$_5$-C$_{10}$)heterocyclyl, N(C$_1$-C$_6$)alkyl-C(O)—(C$_1$-C$_6$)alkyl, N(C$_1$-C$_6$)alkyl-C(O)O—(C$_1$-C$_6$)alkyl, N(C$_1$-C$_6$)alkyl-C(O)—NH—(C$_1$-C$_6$)alkyl], (C$_6$-C$_{10}$)aryl, (C$_1$-C$_6$)alkylene-(C$_6$-C$_{10}$)aryl, O—(C$_6$-C$_{10}$)aryl, O—(C$_1$-C$_6$)alkylene-(C$_6$-C$_{10}$)aryl, (C$_5$-C$_{10}$)heterocyclyl, (C$_1$-C$_6$)alkylene-(C$_5$-C$_{10}$)heterocyclyl, and O—(C$_1$-C$_6$)alkylene-(C$_5$-C$_{10}$)heterocyclyl, wherein the (C$_6$-C$_{10}$)aryl or (C$_5$-C$_{10}$)heterocyclyl in the substituent may be substituted one to three times by a group independently selected from halogen, OH, NO$_2$, CN, O—(C$_1$-C$_6$)alkyl, (C$_1$-C$_6$)alkyl, NH$_2$, NH(C$_1$-C$_6$)alkyl, N[(C$_1$-C$_6$)alkyl]$_2$, SO$_2$CH$_3$, COOH, C(O)O—(C$_1$-C$_6$)alkyl, CONH$_2$, (C$_1$-C$_6$)alkylene-O—(C$_1$-C$_6$)alkyl, (C$_1$-C$_6$)alkylene-O—(C$_6$-C$_{10}$)aryl and O—(C$_1$-C$_6$)alkylene-(C$_6$-C$_{10}$)aryl; or wherein (C$_6$-C$_{10}$)aryl is vicinally substituted by a O—(C$_1$-C$_4$)alkylene-O group whereby a 5-8-membered ring is formed together with the carbon atoms the oxygen atoms are attached to; and wherein aryl substituent of (C$_6$-C$_{10}$)aryl and (C$_5$-C$_{10}$)heterocyclyl substituent groups may not be further substituted by an aryl or heterocyclyl containing group; or
stereoisomeric form thereof and/or tautomeric form thereof and/or pharmaceutically acceptable salt thereof.

DETAILED DESCRIPTION OF THE INVENTION

Definitions

The terms (C$_1$-C$_2$)alkyl, (C$_1$-C$_4$)alkyl, (C$_1$-C$_6$)alkyl, (C$_1$-C$_8$)alkyl and the corresponding alkylene substituents are understood as a hydrocarbon residue which can be linear, i.e. straight-chain, or branched and has 1, 2, 3, 4, 5, 6, 7 or 8 carbon atoms, respectively. This also applies if an alkyl group occurs as a substituent on another group, for example in an alkoxy group (O-alkyl), S-alkyl or a —O($C_1$-$C_6$)alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl or alkylene groups may—if not otherwise stated—be halogenated once or more, e.g. alkyl groups may be fluorinated, e.g. perfluorinated. Examples of halogenated alkyl groups are $CF_3$ and $CH_2CF_3$, $OCF_3$, $SCF_3$, or —O—$(CF_2)_2$—O—.

The term ($C_2$-$C_6$)-alkenyl means a hydrocarbon residue whose carbon chain is straight-chain or branched and comprises 2 to 6 carbon atoms and have, depending on the chain length, 1, 2 or 3 double bonds, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. The double bond may where possible have the E or Z orientation. The double bonds may be both internal and terminal.

($C_2$-$C_6$)-alkynyl groups are hydrocarbon radicals whose carbon chain is straight-chain or branched and comprises 2 to 6 carbon atoms and have, depending on the chain length, 1 or 2 triple bonds, for example, ethynyl, 1-propynyl, 2-propynyl (=propargyl) or 2-butynyl. The triple bonds may be both internal and terminal.

Halogen means fluoro, chloro, bromo or iodo.

($C_3$-$C_8$)cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A ($C_6$-$C_{10}$)aryl group means an aromatic ring or a ring system which comprises two aromatic rings which are fused or otherwise linked, for example a phenyl, naphthyl, biphenyl, tetrahydronaphthyl, alpha- or beta-tetralon-, indanyl- or indan-1-on-yl group. A preferred ($C_6$-$C_{10}$)aryl group is phenyl.

A ($C_5$-$C_{10}$)heterocyclyl group means a mono- or bicyclic ring system in which one or more carbon atoms can be replaced by one or more heteroatoms such as, for example 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position. ($C_5$-$C_{10}$)heterocyclyl groups may be (1) aromatic [=heteroaryl groups] or (2) saturated or (3) mixed aromatic/saturated.

Suitable ($C_5$-$C_{10}$)heterocyclyl group include acridinyl, azocinyl, benzimidazolyl, benzofuryl, benzomorpholinyl, benzothienyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, furanyl, quinazolinyl, quinolinyl, 4H-quinolizinyl, quinoxalinyl, quinuclidinyl, chromanyl, chromenyl, chromen-2-onyl, cinnolinyl, decahydroquinolinyl, 2H,6H-1,5,2-dithiazinyl, dihydrofuro[2,3-b]-tetrahydrofuran, furyl, furazanyl, homomorpholinyl, homopiperazinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, prolinyl, pteridinyl, purynyl, pyranyl, pyrazinyl, pyroazolidinyl, pyrazolinyl, pyrazolyl, pyridazinyl, pyridonyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl. Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in ($C_5$-$C_{10}$)heterocyclyl residues can occur on free carbon atoms or on nitrogen atoms.

Preferred examples of ($C_5$-$C_{10}$)heterocyclyl residues are pyrazinyl, pyridyl, pyrimidinyl, pyrazolyl, morpholinyl, pyrrolidinyl, piperazinyl, piperidinyl, thienyl, benzofuryl, quinolinyl, tetrazolyl and triazolyl.

($C_6$-$C_{10}$)aryl and ($C_5$-$C_{10}$)heterocyclyl groups are unsubstituted or, if not stated otherwise, substituted one or more times, preferably one to three times, by suitable groups independently selected from halogen, OH, $NO_2$, $N_3$, CN, C(O)—($C_1$-$C_6$)alkyl, C(O)—($C_6$-$C_{10}$)aryl, COOH, COO($C_1$-$C_6$)alkyl, $CONH_2$, CONH($C_1$-$C_6$)alkyl, CON[($C_1$-$C_6$)alkyl]$_2$, ($C_3$-$C_8$)cycloalkyl, ($C_1$-$C_6$)alkyl, ($C_1$-$C_6$)alkylene-OH, ($C_1$-$C_6$)alkylene-$NH_2$, ($C_1$-$C_6$)alkylene-NH($C_1$-$C_6$)alkyl, ($C_1$-$C_6$)alkylene-N[($C_1$-$C_6$)alkyl]$_2$, ($C_2$-$C_6$)alkenyl, ($C_2$-$C_6$)alkynyl, O—($C_1$-$C_6$)alkyl, O—C(O)—($C_1$-$C_6$)alkyl, $PO_3H_2$, $SO_3H$, $SO_2$—$NH_2$, $SO_2$NH($C_1$-$C_6$)alkyl, $SO_2$N[($C_1$-$C_6$)alkyl]$_2$, S—($C_1$-$C_6$)alkyl; SO—($C_1$-$C_6$)alkyl, $SO_2$—($C_1$-$C_6$)alkyl, $SO_2$—N=CH—N[($C_1$-$C_6$)alkyl]$_2$, C(NH)($NH_2$), $NH_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$)alkyl, NH—$SO_2$—($C_1$-$C_6$)alkyl, NH—$SO_2$—($C_6$-$C_{10}$)aryl, NH—$SO_2$—($C_5$-$C_{10}$)heterocyclyl, N($C_1$-$C_6$)alkyl-C(O)—($C_1$-$C_6$)alkyl, N($C_1$-$C_6$)alkyl-C(O)O—($C_1$-$C_6$)alkyl, N($C_1$-$C_6$)alkyl-C(O)—NH—($C_1$-$C_6$)alkyl], ($C_6$-$C_{10}$)aryl, ($C_1$-$C_6$)alkylene-($C_6$-$C_{10}$)aryl, O—($C_6$-$C_{10}$)aryl, O—($C_1$-$C_6$)alkylene-($C_6$-$C_{10}$)aryl, ($C_5$-$C_{10}$)heterocyclyl, ($C_1$-$C_6$)alkylene-($C_5$-$C_{10}$)heterocyclyl, O—($C_1$-$C_6$)alkylene-($C_5$-$C_{10}$)heterocyclyl, wherein the ($C_6$-$C_{10}$)aryl or ($C_5$-$C_{10}$)heterocyclyl may be substituted one to 3 times by a group independently selected from halogen, OH, $NO_2$, CN, O—($C_1$-$C_6$)alkyl, ($C_1$-$C_6$)alkyl, $NH_2$, NH($C_1$-$C_6$)alkyl, N[($C_1$-$C_6$)alkyl]$_2$, $SO_2CH_3$, COOH, C(O)O—($C_1$-$C_6$)alkyl, $CONH_2$, ($C_1$-$C_6$)alkylene-O—($C_1$-$C_6$)alkyl, ($C_1$-$C_6$)alkylene-O—($C_6$-$C_{10}$)aryl, O—($C_1$-$C_6$)alkylene-($C_6$-$C_{10}$)aryl; or wherein ($C_6$-$C_{10}$)aryl is vicinally substituted by a O—($C_1$-$C_4$)alkylene-O group whereby a 5-8-membered ring is formed together with the carbon atoms the oxygen atoms are attached to. Aryl or heterocyclyl substituents of ($C_6$-$C_{10}$)aryl and ($C_5$-$C_{10}$)heterocyclyl groups may not be further substituted by an aryl or heterocyclyl containing group.

Preferred substituents for ($C_6$-$C_{10}$)aryl groups are ($C_1$-$C_4$)alkyl, O—($C_1$-$C_4$)alkyl, O-phenyl, phenyl, C(O)O—($C_1$-$C_6$)alkyl, C(O)OH, C(O)—($C_1$-$C_4$)alkyl, halogen, $NO_2$, $SO_2NH_2$, CN, $SO_2$—($C_1$-$C_4$)alkyl, $SO_2$—N=CH—N[($C_1$-$C_6$)alkyl]$_2$, NH—$SO_2$—($C_1$-$C_4$)alkyl, $NH_2$, NH—C(O)—($C_1$-$C_4$)alkyl, ($C_3$-$C_8$)cycloalkyl, ($C_1$-$C_4$)alkyl-OH, C(O)N[($C_1$-$C_4$)alkyl]$_2$, CONH($C_1$-$C_4$)alkyl, C(O)$NH_2$, N[($C_1$-$C_4$)alkyl]$_2$, ($C_1$-$C_4$)alkylene-($C_6$-$C_{10}$)aryl, wherein the ($C_6$-$C_{10}$)aryl may be further substituted one to three times, preferably once, by ($C_1$-$C_4$)alkyl, ($C_1$-$C_4$)alkylene-O—($C_1$-$C_6$)alkyl, $(C_6-C_{10})$aryl O—$(C_1-C_6)$alkyl-$(C_6-C_{10})$aryl, or may be vicinally substituted by a O—$(C_1-C_4)$alkylene-O group whereby a 5-8-membered ring is formed together with the carbon atoms the oxygen atoms are attached to. More preferred substituents for $(C_6-C_{10})$aryl are halogen, CN, phenyl, O-phenyl, NH—C(O)—$(C_1-C_4)$alkyl especially NH—C(O)—$CH_3$, C(O)—$(C_1-C_4)$alkyl especially C(O)—$CH_3$, $(C_1-C_4)$alkyl especially $CH_3$ or $CF_3$, O—$(C_1-C_4)$alkyl especially O—$CH_3$, $SO_2$—$NH_2$, $SO_2$—$(C_1-C_4)$alkyl especially $SO_2$—$CH_3$ or $SO_2$—$CF_3$ or $SO_2$—N=CH—N[$(C_1-C_4)$alkyl]$_2$ especially $SO_2$—N=CH—N[$(CH3)_2$.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

Preferred substituents for $(C_5-C_{10})$heterocyclyl groups are $(C_1-C_4)$alkyl, O—$(C_1-C_4)$alkyl, $(C_1-C_4)$alkylene-phenyl, halogen, $(C_1-C_4)$alkylene-O—$(C_1-C_4)$alkyl, $(C_5-C_{10})$heterocyclyl, $(C_1-C_4)$alkylene-N[$(C_1-C_4)$alkyl]$_2$, or $(C_6-C_{10})$aryl, wherein the $(C_6-C_{10})$aryl may be further substituted by $(C_1-C_4)$alkyl, O—$(C_1-C_6)$alkyl, halogen, $(C_1-C_4)$alkylene-O—$(C_1-C_6)$alkyl, O—$(C_1-C_6)$alkyl-$(C_6-C_{10})$aryl, or may be vicinally substituted by a O—$(C_1-C_4)$alkylene-O group whereby a 5-8-membered ring is formed together with the carbon atoms the oxygen atoms are attached to. More preferred substituents for $(C_5-C_{10})$heterocyclyl groups are $(C_1-C_4)$alkyl, halogen or phenyl, wherein the phenyl may be further substituted one to three times, preferably once, by halogen, $(C_1-C_4)$ alkyl or O—$(C_1-C_4)$alkyl.

The general and preferred substituents of $(C_6-C_{10})$aryl and $(C_5-C_{10})$heterocyclyl groups may be combined with the general and preferred definitions of $R_1$, $R_2$, $R_3$, $R_4$, $R_5$, $R_6$, $R_7$, $R_8$, n, m, L and p as described above.

Embodiments

In one embodiment of the present invention $R_1$ is H, the compound is thus characterized by the formula (II)

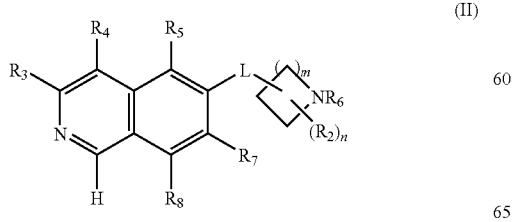

(II)

In another embodiment $R_1$ is OH, the compound is thus characterized by the formula (III)

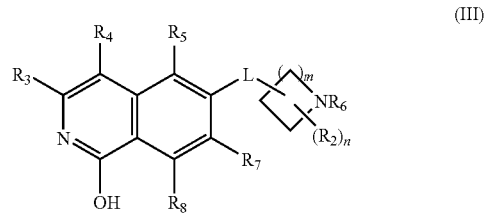

(III)

The compound of formula (III) has a tautomeric form of the formula (III')

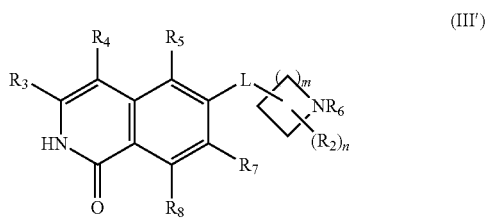

(III')

The tautomeric form is also an embodiment of the present invention.

In a further embodiment $R_1$ is $NH_2$ and the compound has the formula (IV)

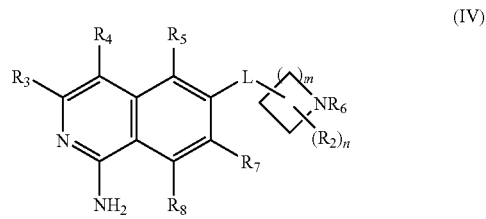

(IV)

$R_1$ is preferably H or OH.

$R_3$ is preferably H, halogen, $(C_1-C_4)$alkylene-R', O—R" or NHR". More preferred, $R_3$ is H or NHR". Most preferred, $R_3$ is H, NH—$(C_5-C_6)$heterocyclyl or NH-phenyl, especially preferred are H, NH—$(C_5-C_6)$heteroaryl containing one or more N atoms or NH-phenyl. Most especially preferred, $R_3$ is H.

Examples of $R_3$ substituents are

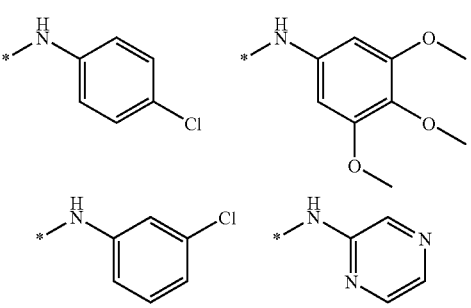

Preferably, $R_4$ is H, halogen or $(C_1-C_6)$alkyl. More preferred, $R_4$ is H, halogen or $(C_1-C_4)$alkyl. Most preferred, $R_4$ is H.

Preferably, $R_5$ is H, halogen, CN, $(C_1-C_6)$alkyl, $(C_2-C_6)$alkenyl, R', NH—$(C_6-C_{10})$aryl or $(C_1-C_6)$alkylene-R'. More preferably, $R_5$ is H, halogen, $(C_1-C_6)$alkyl, $(C_2-C_6)$alkenyl, R', NH—$(C_6-C_{10})$aryl or $(C_1-C_6)$alkylene-R'. Most preferably, $R_5$ is H, halogen, $(C_1-C_6)$alkyl, $(C_2-C_6)$alkenyl, $(C_6-C_{10})$aryl, NH—$(C_6-C_{10})$aryl, $(C_1-C_2)$alkyl-$(C_6-C_{10})$aryl or $(C_5-C_{10})$heteroaryl. Especially preferred, $R_5$ is H, halogen, phenyl, $(C_1-C_6)$alkyl, $(C_2-C_6)$alkenyl, $(C_6-C_{10})$aryl or $(C_5-C_6)$heteroaryl. Most especially preferred $R_5$ is H, halogen, methyl, ethyl, vinyl, phenyl, thienyl or pyridyl.

Examples of $R_5$ are hydrogen, fluoro, chloro, bromo, iodo, methyl, ethyl, vinyl, phenyl, thienyl or pyridyl, nitrile, nitro, (p-methoxy)-phenyl, N-aniline, benzyl, 2-propenyl, s-butenyl, cyclopropyl, tetrazol, amino, 4-methoxy-aniline or N-acetyl, preferably hydrogen, fluoro, chloro, bromo, iodo, methyl, ethyl, vinyl, phenyl, thienyl or pyridyl More preferred, $R_5$ is H, halogen, methyl, or ethyl, most preferred $R_5$ is H.

Preferably, $R_6$ is H, $(C_1-C_6)$alkyl, R', $(C_1-C_4)$alkylene-$(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_6)$alkylene-O—$(C_1-C_6)$alkyl, $(C_1-C_4)$alkylene-C(O)—$(C_5-C_{10})$heterocyclyl, $(C_1-C_4)$alkylene-C(O)—$(C_6-C_{10})$aryl, $(C_1-C_6)$alkylene-C(O)N[$(C_1-C_6)$alkyl]$_2$, $(C_1-C_6)$alkylene-C(O)NH—$(C_1-C_6)$alkyl, $(C_1-C_6)$alkylene-C(O)O—$(C_1-C_6)$alkyl, C(O)O—$(C_1-C_6)$alkyl, C(O)$(C_1-C_6)$alkyl, C(O)R', C(O)NH—$(C_1-C_6)$alkyl, C(O)N[$(C_1-C_6)$alkyl]$_2$, or C(O)$(C_1-C_6)$alkylene-R'.

In a further preferred embodiment $R_6$ is H, $(C_1-C_6)$alkyl, $(C_5-C_{10})$heterocyclyl, $(C_3-C_8)$cycloalkyl, $(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_6)$alkylene-O—$(C_1-C_6)$alkyl, $(C_1-C_6)$alkylene-C(O)N[$(C_1-C_6)$alkyl]$_2$, $(C_1-C_6)$alkylene-C(O)NH—$(C_1-C_6)$alkyl, $(C_1-C_6)$alkylene-C(O)O—$(C_1-C_6)$alkyl, C(O)O—$(C_1-C_6)$alkyl, C(O)$(C_1-C_6)$alkyl, C(O)—$(C_5-C_{10})$heterocyclyl, C(O)$(C_3-C_8)$cycloalkyl, C(O)NH—$(C_1-C_6)$alkyl, C(O)N[$(C_1-C_6)$alkyl]$_2$, C(O)$(C_1-C_6)$alkylene-$(C_3-C_8)$cycloalkyl, C(O)$(C_1-C_6)$alkylene-$C_5-C_{10}$)heterocyclyl, or C(O)$(C_1-C_6)$alkylene-$(C_6-C_{10})$aryl.

In a further more preferred embodiment $R_6$ is H, $(C_1-C_6)$alkyl, $(C_3-C_8)$cycloalkyl, $(C_5-C_{10})$heterocyclyl, $(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_6)$alkylene-O—$(C_1-C_6)$alkyl, $(C_1-C_6)$alkylene-C(O)NH—$(C_1-C_6)$alkyl, $(C_1-C_6)$alkylene-C(O)N[$(C_1-C_6)$alkyl]$_2$, C(O)O—$(C_1-C_6)$alkyl, C(O)$(C_1-C_6)$alkyl, C(O)$(C_3-C_8)$cycloalkyl, C(O)—$(C_5-C_{10})$heterocyclyl, C(O)NH—$(C_1-C_6)$alkyl, C(O)N[$(C_1-C_6)$alkyl]$_2$, C(O)$(C_1-C_6)$alkylene-$(C_3-C_8)$cycloalkyl, C(O)$(C_1-C_6)$alkylene-$(C_5-C_{10})$heterocyclyl, or C(O)$(C_1-C_6)$alkylene-$(C_6-C_{10})$aryl.

In an more preferred embodiment $R_6$ is H, $(C_1-C_6)$alkyl, $(C_3-C_8)$cycloalkyl, $(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_4)$alkylene-O—$(C_1-C_4)$alkyl, C(O)$(C_1-C_6)$alkyl, C(O)$(C_3-C_8)$cycloalkyl, C(O)—$(C_5-C_{10})$heterocyclyl, C(O)$(C_1-C_4)$alkylene-$(C_5-C_{10})$heterocyclyl, or C(O)$(C_1-C_4)$alkylene-$(C_6-C_{10})$aryl.

In an even more preferred embodiment $R_6$ is
H,
$(C_1-C_6)$alkyl,
$(C_3-C_8)$cycloalkyl;
$(C_1-C_4)$alkylene-$(C_3-C_8)$cycloalkyl;

$(C_1-C_4)$alkylene-$(C_5-C_{10})$heterocyclyl wherein heterocyclyl is unsubstituted or substituted one or more times, preferably one or two times, by $(C_1-C_4)$alkyl;

$(C_1-C_4)$alkylene-$(C_6-C_{10})$aryl wherein aryl is unsubstituted or substituted one or more times, preferably one to three times, by halogen, $(C_1-C_4)$alkyl especially $CH_3$ or $CF_3$, O—$(C_1-C_4)$alkyl especially $OCH_3$, $SO_2$—$(C_1-C_4)$alkyl especially $S(O)_2CH_3$ or $SO_2CF_3$, or $SO_2$—N=CH—N[$(C_1-C_6)$alkyl]$_2$ especially $SO_2$—N=CH—N$(CH_3)_2$.

Especially preferred $R_6$ is H, $(C_1-C_6)$alkyl or $(C_3-C_8)$cycloalkyl. In an even more especially preferred embodiment $R_6$ is H, preferably unsubstituted $(C_1-C_6)$alkyl or preferably unsubstituted $(C_3-C_8)$cycloalkyl. Most preferred $R_6$ is H.

As examples for these embodiments, $R_6$ is hydrogen, methyl, ethyl, propyl, isopropyl, 3-methyl-butyl, 2-methyl-propyl, 1-ethyl-propyl, butyl, pentyl, 3,3,3-trifluoropropyl, 4,4,4-trifluorobutyl or a substituent selected from the group consisting of

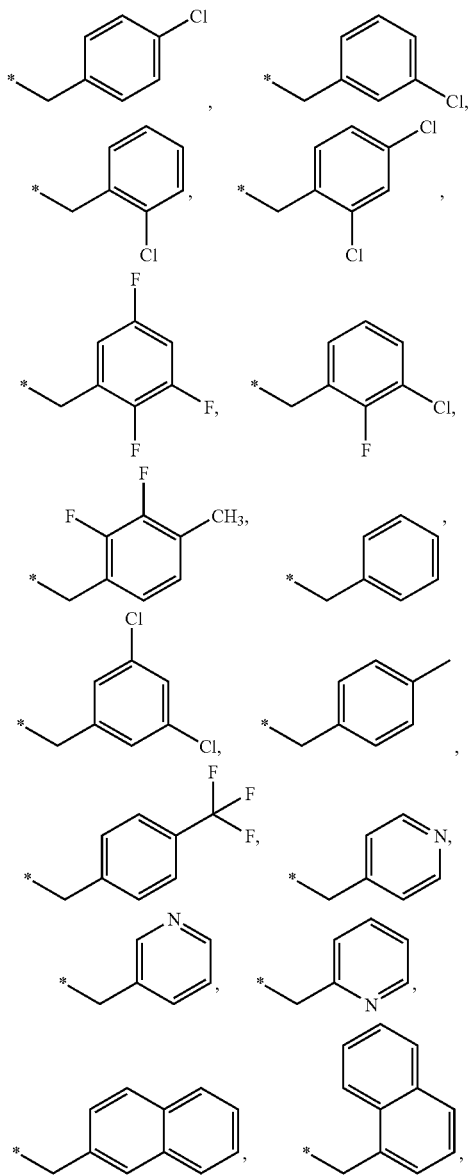

The asterisk (*) denotes where the bond is connected to the N-atom of the ring.

Preferably, $R_7$ is H, halogen, CN, $(C_1-C_6)$alkyl, O—$(C_1-C_6)$alkyl, $(C_2-C_6)$alkenyl, R' or $(C_1-C_6)$alkylene-$(C_3-C_8)$cycloalkyl. More preferred, $R_7$ is H, halogen, CN, $(C_1-C_4)$alkyl, O—$(C_1-C_4)$alkyl, $(C_2-C_4)$alkenyl, phenyl, cyclopropyl or $(C_5-C_6)$heteroaryl. Most preferably, $R_7$ is H, fluoro, chloro, bromo, methyl, ethyl, methoxy, propyl, phenyl, nitrile, cyclopropyl, thienyl or vinyl, most especially preferred $R_7$ is H, fluoro, chloro, bromo, methyl, propyl or methoxy. Most preferred $R_7$ is H. $R_8$ is preferably H, halogen or $(C_1-C_4)$alkyl. More preferred, $R_8$ is H, Cl, F, methyl or ethyl. Most preferred $R_8$ is H.

Preferably, $R_2$ is
R',
$(C_7-C_8)$alkyl,
$(C_1-C_6)$alkylene-R',
$(C_2-C_6)$alkenyl,
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
C(O)NH—$(C_1-C_6)$alkyl,
C(O)NHR',
C(O)—NH$(C_2-C_6)$alkenyl,
C(O)—NH$(C_1-C_6)$alkynyl,
C(O)—NH$(C_1-C_6)$alkylene-R',
C(O)N[$(C_1-C_6)$alkyl]R'
C(O)N[$(C_1-C_6)$alkyl]$_2$,
C(O)—$(C_1-C_6)$alkylene-R',
C(O)O$(C_1-C_6)$alkylene-R';
or $R_2$ is $(C_1-C_6)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
or $R_2$ is a $(C_1-C_4)$alkylene bound to the cyclic amine, in which the $(C_1-C_4)$alkylene forms a second bond to a different carbon atom of the cyclic amine ring and forms, together with carbon atoms of cyclic amine, a second, 4-8 membered ring;
More preferably, $R_2$ is
R',
$(C_1-C_6)$alkylene-R',
$(C_2-C_6)$alkenyl,
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
C(O)NH—$(C_1-C_6)$alkyl,
C(O)NHR',
C(O)—NH$(C_2-C_6)$alkynyl,
C(O)—NH$(C_1-C_6)$alkylene-R',
or $R_2$ is $(C_1-C_3)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
or $R_2$ is a $(C_1-C_4)$alkylene bound to the cyclic amine, in which the $(C_1-C_4)$ alkylene forms a second bond to a different carbon atom of the cyclic amine ring and forms, together with carbon atoms of cyclic amine, a second, 4-8 membered ring.

Most preferably, $R_2$ is
R',
$(C_1-C_6)$alkylene-R',
$(C_2-C_6)$alkenyl,
$(C_1-C_6)$alkylene-C(O)NH—R',
$(C_1-C_6)$alkylene-C(O)NH—$(C_1-C_6)$alkyl,
C(O)NH—$(C_1-C_6)$alkyl,
C(O)NHR',
C(O)—NH$(C_2-C_6)$alkynyl,
C(O)—NH$(C_1-C_6)$alkylene-R',
or $R_2$ is a $(C_1-C_2)$alkylene bound to the cyclic amine, in which the $(C_1-C_4)$alkylene forms a second bond to a different carbon atom of the cyclic amine ring and forms, together with carbon atoms of cyclic amine, a second, 4-8 membered ring;

$R_2$ may be bound to any carbon atom of the ring including the position where the linker group L is bound.

As examples for these embodiments, $R_2$ is

The asterisk (*) denotes where the bond is connected to the C-atom of the ring.

Examples for the embodiments wherein $R_2$ is a $C_1-C_4$ alkylene, which creates a second ring system with the cyclic amine, comprise in a preferred embodiment the created ring system is selected from More preferred, it is one of Preferably, n is 1, 2 or 3. More preferred, n is 1 or 2. Most preferred n is 1.

Preferably m is 2, 3 or 4. More preferred m is 3.

The linker group L may be bound to the ring in any position via a ring carbon atom. In a preferred embodiment, m is 3 and L is attached to the 4-position of the piperidine ring or L is attached to the 3-position of the piperidine ring

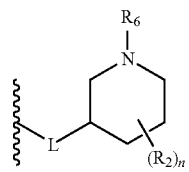

in all their stereochemical forms.

In an especially preferred embodiment, L is attached to the 4-position of the piperidine ring.

In another embodiment, L is O—(CH$_2$)p. In a further embodiment of L, L is S(CH$_2$)p, S(O)(CH$_2$)p or SO$_2$(CH$_2$)p. In another embodiment L is NH(CH$_2$)p, N(C$_1$-C$_6$)alkyl-(CH$_2$)p, N(C$_3$-C$_6$)cycloalkyl-(CH$_2$)p N[CO(C$_1$-C$_6$)alkyl]-(CH$_2$)p, N[(C$_1$-C$_3$)alkylene-aryl]-(CH$_2$)p or N[(C$_1$-C$_3$)alkylene-(C$_5$-C$_6$)heterocyclyl]-(CH$_2$)p with NH(CH$_2$)p, N(C$_1$-C$_6$)alkyl-(CH$_2$)p being more preferred. A preferred N(C$_1$-C$_6$) alkyl is N(C$_1$-C$_4$)alkyl, more preferably NCH$_3$ or NCH$_2$CH$_3$ with NCH$_3$ being more preferred. Even more preferred L is O—(CH$_2$)p, S(CH$_2$)p or NH(CH$_2$)p. Most preferred L is O, S or NH with O being especially preferred.

Preferably p is 0, 1, 2, or 3, more preferred 0 or 1, with 0 being most preferred.

More preferably, m is 3 and L is O, S or NH and is attached to the 4-position of the piperidine ring.

In residues R$_2$ to R$_8$ an alkyl or alkylene can optionally be substituted one or more times by halogen. Preferably alkyl or alkylene is substituted one to three times by halogen selected from chloro or bromo but may be substituted by fluoro once or more, e.g. being perfluorinated. Preferably halogen is Fluor. More preferred an alkyl or alkylene is not halogenated.

In residues R$_2$, R$_4$, R$_5$, R$_6$, R$_7$ and R$_8$ alkyl, alkylene or cycloalkyl can optionally be substituted one or more times by a group selected independently from OH, OCH$_3$, COOH, COOCH$_3$, NH$_2$, NHCH$_3$, N(CH$_3$)$_2$, CONH$_2$, CONHCH$_3$ or CON(CH$_3$)$_2$. If substituted, the number of substituents is preferably between 1, 2, 3 or 4, more preferably 1 or 2 with 1 being even more preferred. Preferably an alkylene or cycloalkyl is not substituted. More preferably an alkyl, alkylene or cycloalkyl is not substituted. Preferably in R$_4$, R$_5$, R$_7$ and R$_8$ an alkyl, alkylene or cycloalkyl is not substituted. More preferred, in R$_4$, R$_5$, R$_6$, R$_7$ and R$_8$ an alkyl, alkylene or cycloalkyl is not substituted.

In preferred embodiments of the present invention one or more or all of the groups contained in the compounds of formula (I) can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formula (I) in all stereoisomeric forms and mixtures of stereoisomeric forms in all ratios, and their pharmaceutically acceptable salts.

The term "*-" in the exemplified substituents vide supra marks the point where the substituent is attached, which means, for example, for a R$_3$ substituent

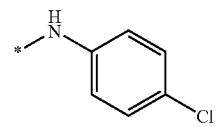 [SMILES: *Nc1ccc(Cl)cc1]

and m is 3 and R$_1$ is H a compound of the formula

A preferred embodiment is a compound of the formula (I) wherein
R$_1$ is H, OH or NH$_2$;
R$_2$ is
R',
(C$_7$-C$_8$)alkyl,
(C$_1$-C$_6$)alkylene-R',
(C$_2$-C$_6$)alkenyl,
(C$_1$-C$_6$)alkylene-C(O)NH$_2$,
(C$_1$-C$_6$)alkylene-C(O)NH—R',
(C$_1$-C$_6$)alkylene-C(O)NH—(C$_1$-C$_6$)alkyl,
(C$_1$-C$_6$)alkylene-C(O)N[(C$_1$-C$_6$)alkyl]$_2$,
(C$_1$-C$_6$)alkylene-C(O)N[R']$_2$;
(C$_1$-C$_6$)alkylene-C(O)O—(C$_1$-C$_6$)alkyl,
C(O)NH—(C$_1$-C$_6$)alkyl,
C(O)NHR',
C(O)—NH(C$_2$-C$_6$)alkenyl,
C(O)—NH(C$_2$-C$_6$)alkynyl,
C(O)—NH(C$_1$-C$_6$)alkylene-R',
C(O)N[(C$_1$-C$_6$)alkyl]R'
C(O)N[(C$_1$-C$_6$)alkyl]$_2$,
C(O)—(C$_1$-C$_6$)alkylene-R',
C(O)O(C$_1$-C$_6$)alkylene-R';
or R$_2$ is (C$_1$-C$_6$)alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
or R$_2$ is a (C$_1$-C$_4$)alkylene bound to the cyclic amine, in which the (C$_1$-C$_4$) alkylene forms a second bond to a different carbon atom of the cyclic amine ring and forms, together with carbon atoms of cyclic amine, a second, 4-8 membered ring;
R$_3$ is H, halogen, (C$_1$-C$_4$)alkylene-R', O—R" or NHR";
R$_4$ is H, halogen or (C$_1$-C$_6$)alkyl;
R$_5$ is H, (C$_1$-C$_6$)alkyl, halogen, CN, (C$_2$-C$_6$)alkenyl, (C$_6$-C$_{10}$) aryl, NH—(C$_6$-C$_{10}$)aryl, (C$_1$-C$_6$)alkylene-(C$_6$-C$_{10}$)aryl, (C$_5$-C$_{10}$)heterocyclyl or (C$_1$-C$_6$)alkylene-(C$_5$-C$_{10}$)heterocyclyl;
R$_6$ is H, R', (C$_1$-C$_8$)alkyl, (C$_1$-C$_6$)alkylene-R', (C$_1$-C$_6$)alkylene-O—(C$_1$-C$_6$)alkyl, (C$_1$-C$_6$)alkylene-O—R', (C$_1$-C$_6$)alkylene-CH[R']$_2$, (C$_1$-C$_6$)alkylene-C(O)NH$_2$, (C$_1$-C$_6$)alkylene-C(O)NH—R', (C$_1$-C$_6$)alkylene-C(O)N[(C$_1$-C$_4$)alkyl]$_2$, C(O)(C$_1$-C$_4$)alkyl or (C$_1$-C$_6$)alkylene-C(O)N[R']$_2$,
C(O)O—(C$_1$-C$_6$)alkyl, C(O)(C$_1$-C$_6$)alkyl, C(O)(C$_3$-C$_8$)cycloalkyl, C(O)NH—(C$_1$-C$_6$)alkyl, C(O)N[(C$_1$-C$_6$)alkyl]$_2$, C(O)(C$_1$-C$_6$)alkylene-C$_3$-C$_8$)cycloalkyl, C(O)(C$_1$-C$_6$)alkylene-C$_5$-C$_{10}$)heterocyclyl or C(O)(C$_1$-C$_6$)alkylene-(C$_6$-C$_{10}$)aryl.
R$_7$ is H, halogen, CN, (C$_1$-C$_6$)alkyl, O—(C$_1$-C$_6$)alkyl, (C$_2$-C$_6$)alkenyl or R';
R$_8$ is H, halogen or (C$_1$-C$_6$)alkyl;
m is 2, 3 or 4
n is 1, 2 or 3,
L is S(CH$_2$)p, NH(CH$_2$)p or N(C$_1$-C$_6$)alkyl-(CH$_2$)p, and
p is 0, 1 or 2;
or their stereoisomeric and/or tautomeric forms and/or their pharmaceutically acceptable salts.

A further preferred embodiment is a compound of the formula (I) wherein
R$_1$ is H or OH;
R$_2$ is
R',
(C$_1$-C$_6$)alkylene-R',
(C$_2$-C$_6$)alkenyl,
(C$_1$-C$_6$)alkylene-C(O)NH$_2$,
(C$_1$-C$_6$)alkylene-C(O)NH—R',
(C$_1$-C$_6$)alkylene-C(O)NH—(C$_1$-C$_6$)alkyl,
C(O)NH—(C$_1$-C$_6$)alkyl,
C(O)NHR',
C(O)—NH(C$_1$-C$_6$)alkylene-R',
C(O)—NH(C$_2$-C$_6$)alkenyl,
C(O)—NH(C$_2$-C$_6$)alkynyl,
or R$_2$ is (C$_1$-C$_4$)alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
or R$_2$ is a (C$_1$-C$_4$)alkylene bound to the cyclic amine, in which the (C$_1$-C$_4$) alkylene forms a second bond to a different carbon atom of the cyclic amine ring and forms, together with carbon atoms of cyclic amine, a second, 4-8 membered ring;
R$_3$ is H, halogen or NHR";
R$_4$ is H, halogen or (C$_1$-C$_4$)alkyl;
R$_5$ is H, (C$_1$-C$_6$)alkyl, halogen, (C$_2$-C$_4$)alkenyl, (C$_6$-C$_{10}$)aryl, (C$_1$-C$_6$)alkylene-(C$_6$-C$_{10}$)aryl or (C$_5$-C$_{10}$)heterocyclyl;
R$_6$ is H, (C$_3$-C$_8$)cycloalkyl, (C$_1$-C$_8$)alkyl, (C$_1$-C$_6$)alkylene-O—(C$_1$-C$_6$)alkyl, (C$_1$-C$_3$)alkylene-R', C(O)O—(C$_1$-C$_6$)alkyl, C(O)(C$_1$-C$_6$)alkyl, C(O)(C$_3$-C$_8$)cycloalkyl, C(O)—(C$_5$-C$_{10}$)heterocyclyl, C(O)NH—(C$_1$-C$_6$)alkyl, C(O)N[(C$_1$-C$_6$)alkyl]$_2$, C(O)(C$_1$-C$_3$)alkylene-(C$_3$-C$_8$)cycloalkyl, C(O)(C$_1$-C$_3$)alkylene-(C$_5$-C$_{10}$)heterocyclyl, or C(O)(C$_1$-C$_3$)alkylene-(C$_6$-C$_{10}$)aryl;
R$_7$ is H, halogen, CN, (C$_1$-C$_6$)alkyl, O—(C$_1$-C$_6$)alkyl, (C$_2$-C$_6$)alkenyl or R';
R$_8$ is H, halogen or (C$_1$-C$_6$)alkyl;
m is 2, 3 or 4;
n is 1, 2 or 3;
L is O—(CH$_2$)p, S(CH$_2$)p or NH(CH$_2$)p, and
p is 0 or 1;
or their stereoisomeric and/or tautomeric forms and/or their pharmaceutically acceptable salts.

An especially preferred embodiment is a compound of the formula (I) wherein
R$_1$ is H or OH;
R$_2$ is
C$_1$-C$_6$)alkylene-R',
(C$_2$)alkenyl,
(C$_1$-C$_6$)alkylene-C(O)NH—R',
(C$_1$-C$_6$)alkylene-C(O)NH—(C$_1$-C$_6$)alkyl,
C(O)NH—(C$_1$-C$_6$)alkyl,
C(O)—NH(C$_2$-C$_6$)alkynyl,
C(O)NHR',
C(O)—NH(C$_1$-C$_6$)alkylene-R',
or R$_2$ is a (C$_1$-C$_2$)alkylene bound to the cyclic amine, in which the (C$_1$-C$_4$) alkylene forms a second bond to a different carbon atom of the cyclic amine ring and forms, together with carbon atoms of cyclic amine, a second, 4-8 membered ring;
R$_3$ is H, NH—(C$_5$-C$_6$)heteroaryl or NH-phenyl;
R$_4$ is H, halogen or (C$_1$-C$_4$)alkyl;
R$_5$ is H, (C$_1$-C$_4$)alkyl, halogen, (C$_2$-C$_4$)alkenyl, (C$_6$-C$_{10}$)aryl, (C$_1$-C$_2$)alkyl-(C$_6$-C$_{10}$)aryl or (C$_5$-C$_6$)heteroaryl;
R$_6$ is H, (C$_3$-C$_8$)cycloalkyl, (C$_1$-C$_8$)alkyl, (C$_1$-C$_3$)alkylene-R'; C(O)(C$_1$-C$_6$)alkyl, C(O)(C$_3$-C$_8$)cycloalkyl, C(O)—(C$_5$-C$_{10}$)heterocyclyl, C(O)(C$_1$-C$_3$)alkylene-(C$_5$-C$_{10}$)heterocyclyl, or C(O)(C$_1$-C$_3$)alkylene-(C$_6$-C$_{10}$)aryl.
R$_7$ is H, halogen, CN, (C$_1$-C$_4$)alkyl, O—(C$_1$-C$_4$)alkyl, (C$_2$-C$_4$)alkenyl, phenyl, cyclopropyl, (C$_5$-C$_6$)heteroaryl;
R$_8$ is H, halogen or (C$_1$-C$_4$)alkyl;
m is 3
n is 1; and
L is O, S or NH;
or their stereoisomeric and/or tautomeric forms and/or their pharmaceutically acceptable salts.

In an embodiment the present invention relates to a compound of formula (I) selected from the group consisting of
4. (2R,4R)-4-(Isoquinolin-6-yloxy)-piperidine-1,2-dicarboxylic acid 1-tert-butyl ester 2-methyl ester,
8. (2R,4R)-4-(Isoquinolin-6-yloxy)-2-o-tolylcarbamoyl-piperidine-1-carboxylic acid tert-butyl ester,
9. (2R,4R)-4-(Isoquinolin-6-yloxy)-piperidine-2-carboxylic acid o-tolylamide,
10. (2R,4R)-4-(Isoquinolin-6-yloxy)-piperidine-2-carboxylic acid isobutyl-amide,
11. (2R,4R)-4-(Isoquinolin-6-yloxy)-piperidine-2-carboxylic acid 3-methoxy-benzylamide
12. (2R,4R)-4-(Isoquinolin-6-yloxy)-piperidine-2-carboxylic acid 2-chloro-benzylamide
13. (2R,4R)-4-(Isoquinolin-6-yloxy)-piperidine-2-carboxylic acid phenethyl-amide,
14. (2R,4R)-4-(Isoquinolin-6-yloxy)-piperidine-2-carboxylic acid (3-methoxy-propyl)-amide,
15. (2R,4R)-4-(Isoquinolin-6-yloxy)-piperidine-2-carboxylic acid (2-hydroxy-ethyl)-amide,
16. (2R,4R)-4-(Isoquinolin-6-yloxy)-piperidine-2-carboxylic acid (furan-2-ylmethyl)-amide,
17. (2S,4S)-4-(Isoquinolin-6-yloxy)-piperidine-2-carboxylic acid (furan-2-ylmethyl)-amide,
18. (2S,4S)-4-(Isoquinolin-6-yloxy)-piperidine-2-carboxylic acid (3-methoxy-propyl)-amide,
19. (2S,4S)-4-(Isoquinolin-6-yloxy)-piperidine-2-carboxylic acid (pyridin-2-ylmethyl)-amide,
20. (2S,4S)-4-(Isoquinolin-6-yloxy)-piperidine-2-carboxylic acid prop-2-ynylamide,
21. (2S,4S)-4-(Isoquinolin-6-yloxy)-piperidine-2-carboxylic acid phenethyl-amide,
22. (2S,4S)-4-(Isoquinolin-6-yloxy)-piperidine-2-carboxylic acid 2-chloro-benzylamide,
23. (2S,4S)-4-(Isoquinolin-6-yloxy)-piperidine-2-carboxylic acid isobutyl-amide,
24. (2S,4R)-4-(Isoquinolin-6-yloxy)-pyrrolidine-2-carboxylic acid (4-ethyl-phenyl)-amide,
25. (2S,4R)-4-(Isoquinolin-6-yloxy)-pyrrolidine-2-carboxylic acid ((R)-1-phenyl-ethyl)-amide,
26. (2S,4R)-4-(Isoquinolin-6-yloxy)-pyrrolidine-2-carboxylic acid (furan-2-ylmethyl)-amide,
27. (2S,4R)-4-(Isoquinolin-6-yloxy)-pyrrolidine-2-carboxylic acid (2-hydroxy-ethyl)-amide,
28. (2S,4R)-4-(Isoquinolin-6-yloxy)-pyrrolidine-2-carboxylic acid (2-methoxy-ethyl)-amide, 29. (2S,4R)-4-(Isoquinolin-6-yloxy)-pyrrolidine-2-carboxylic acid (3-methoxy-propyl)-amide,
30. (2S,4R)-4-(Isoquinolin-6-yloxy)-pyrrolidine-2-carboxylic acid (pyridin-2-ylmethyl)-amide,
31. (2S,4R)-4-(Isoquinolin-6-yloxy)-pyrrolidine-2-carboxylic acid prop-2-ynylamide,
32. (2S,4R)-4-(Isoquinolin-6-ylamino)-pyrrolidine-1,2-dicarboxylic acid 1-tert-butyl ester 2-methyl ester,
34. (2S,4R)-2-(4-Ethyl-phenylcarbamoyl)-4-(isoquinolin-6-ylamino)-pyrrolidine-1-carboxylic acid tert-butyl ester,
35. (2S,4R)-4-(Isoquinolin-6-ylamino)-pyrrolidine-2-carboxylic acid (4-ethyl-phenyl)-amide,
38. (2S,4R)-4-(Isoquinolin-6-ylamino)-pyrrolidine-2-carboxylic acid (furan-2-ylmethyl)-amide,
39. (2S,4R)-4-(Isoquinolin-6-ylamino)-pyrrolidine-2-carboxylic acid (2-methoxy-ethyl)-amide,
40. (2S,4R)-4-(Isoquinolin-6-ylamino)-pyrrolidine-2-carboxylic acid (3-methoxy-propyl)-amide,
41. (2S,4S)-4-(Isoquinolin-6-ylamino)-pyrrolidine-2-carboxylic acid (furan-2-ylmethyl)-amide,
42. (2S,4S)-4-(Isoquinolin-6-ylamino)-pyrrolidine-2-carboxylic acid (3-methoxy-propyl)-amide,
43. (2S,4S)-4-(Isoquinolin-6-ylamino)-pyrrolidine-2-carboxylic acid (pyridin-2-ylmethyl)-amide,
44. (2S,4S)-4-(Isoquinolin-6-ylamino)-pyrrolidine-2-carboxylic acid (4-ethyl-phenyl)-amide,
45. (2S,4S)-4-(Isoquinolin-6-ylamino)-pyrrolidine-2-carboxylic acid phenethyl-amide,
46. (2S,4S)-4-(Isoquinolin-6-ylamino)-pyrrolidine-2-carboxylic acid 2-chloro-benzylamide,
47. (2S,4S)-4-(Isoquinolin-6-ylamino)-pyrrolidine-2-carboxylic acid isobutyl-amide,
48. (3S,4R)-4-(Isoquinolin-6-ylamino)-pyrrolidine-3-carboxylic acid 3-methoxy-benzylamide,
49. (3S,4R)-4-(Isoquinolin-6-ylamino)-pyrrolidine-3-carboxylic acid (2-methoxy-ethyl)-amide,
50. (3S,4R)-4-(Isoquinolin-6-ylamino)-pyrrolidine-3-carboxylic acid o-tolylamide,
51. (3S,4R)-4-(Isoquinolin-6-ylamino)-pyrrolidine-3-carboxylic acid isobutyl-amide,
52. 6-(8-Methyl-8-aza-bicyclo[3.2.1]oct-3-yloxy)-isoquinoline, or
69. 6-(1-benzyl-4-phenyl-piperidin-4-yloxy)-7-chloro-isoquinoline,
or their stereoisomeric and/or tautomeric forms and/or their pharmaceutically acceptable salts. (Cpd. number given for reference)

In another embodiment the present invention relates to a compound of formula (I) selected from the group consisting of
53  6-(8-Methyl-8-aza-bicyclo[3.2.1]oct-3-yloxy)-2H-isoquinolin-1-one
72/73. 6-(8-Aza-bicyclo[3.2.1]oct-3-yloxy)-7-chloro-2H-isoquinolin-1-one,
74. 6-(8-Methyl-8-aza-bicyclo[3.2.1]oct-3-yloxy)-2H-isoquinolin-1-one,
75. 7-Chloro-6-(8-methyl-8-aza-bicyclo[3.2.1]oct-3-yloxy)-2H-isoquinolin-1-one
76. 7-Methyl-6-(8-methyl-8-aza-bicyclo[3.2.1]oct-3-yloxy)-2H-isoquinolin-1-one, or
77. N6-(4-Amino-4-phenyl-cyclohexyl)-isoquinoline-1,6-diamine,
or their stereoisomeric and/or tautomeric forms and/or their pharmaceutically acceptable salts.

As in any embodiment of the invention, in the preceding embodiments which contain preferred, more preferred, most preferred or exemplary definitions of compounds according to the invention, one or more or all of the groups can have any of its preferred, more preferred, most preferred definitions specified above or any one or some of the specific denotations which are comprised by its definitions and are specified above.

Isoquinoline substitution pattern is numbered according to IUPAC rules:

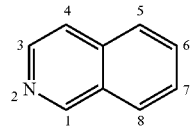

All references to "compound(s) of formula (I)" hereinafter refer to compound(s) of the formula (I), (II), (III), (III') and (IV) as described above, and their pharmaceutically acceptable salts, and/or to their stereoisomeric forms, polymorphs and solvates. Physiologically functional derivatives as described herein are also included.

Pharmaceutically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula (I) of the invention, for example an N-oxide, which on administration to a mammal such as, for example, a human is able to form (directly or indirectly) a compound of the formula (I) or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to compounds of the formula (I), (II), (III), (III') or (VI) in the form of their stereoisomeric forms, which include racemates, racemic mixtures, pure enantiomers and diastereomers and mixtures thereof.

The compounds of the invention may also exist in various polymorphous forms, for example as amorphous and crystalline polymorphous forms. All polymorphous forms of the compounds of the invention belong within the framework of the invention and are a further aspect of the invention.

If radicals or substituents may occur more than once in the compounds of the formula (I), they may all, independently of one another, have the stated meaning and be identical or different.

The present invention therefore also relates to the compounds of the formula (I) and/or their pharmaceutically acceptable salts and/or their prodrugs for use as pharmaceuticals (or medicaments), to the use of the compounds of the formula (I) and/or their pharmaceutically acceptable salts and/or their prodrugs for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, and glaucoma, peripheral circulatory disorder, peripheral occlusive arterial disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

The present invention furthermore relates to pharmaceutical preparations (or pharmaceutical compositions) which contain an effective amount of at least one compound of the formula (I) and/or its pharmaceutically acceptable salts and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

In addition to the active ingredients of the formula (I) and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their pharmaceutically acceptable salts. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physico-chemical properties of the compounds and thus allows the selection of such desired compounds. Furthermore, in addition to at least one compound of the formula (I) and/or its pharmaceutically acceptable salts, the pharmaceutical preparations can also contain one or more other therapeutically or prophylactically active ingredients.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a pharmaceutically acceptable salt or a prodrug of a compound of the formulae (I) can then be carried out by known processes.

In general, a reaction mixture containing a final compound of the formula (I) or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

Accordingly, the following examples are part of and intended to illustrate but not to limit the present invention.

It is understood that modifications that do not substantially affect the activity of the various embodiments of this invention are included within the invention disclosed herein.

| Method A: | |
|---|---|
| Stationary phase: | Col YMC Jsphere 33 × 2 |
| Gradient: | ACN + 0.05% TFA:water + 0.05% TFA |
| | 5:95(0 min) to 95:5(3.4 min) to 95:5(4.4 min) |
| Flow | 1 mL/min |

| Method B: | |
|---|---|
| Stationary phase: | Col YMC Jsphere 33 × 2 |
| Gradient: | ACN + 0.05% TFA:water + 0.05% TFA |
| | 5:95(0 min) to 95:5(2.5 min) to 95:5(3.0 min) |
| Flow | 1 mL/min |

| Method C: | |
|---|---|
| Stationary phase: | Col YMC Jsphere ODS H80 20 × 2 |
| Gradient: | ACN:water + 0.05% TFA |
| | 4:96(0 min) to 95:5(2.0 min) to 95:5(2.4 min) |
| Flow | 1 mL/min |

| Method D: | |
|---|---|
| Stationary phase: | Col YMC Jsphere 33 × 2.1 |
| Gradient: | Grad ACN + 0.08% FA:water + 0.1% FA (Formic Acid) 5:95 (0 min) to 95:5 (2.5 min) to 95:5 (3 min) |
| Flow | 1.3 mL/min |

| Method E: | |
|---|---|
| Stationary phase: | Col YMC Jsphere 33 × 2 |
| Gradient: | ACN + 0.05% TFA:water + 0.05% TFA |
| | 5:95(0 min) to 95:5(2.5 min) to 95:5(3.2 min) |
| Flow | 1.3 mL/min |

| Method F: | |
|---|---|
| Stationary phase: | Col YMC-Pack Pro C18 RS 33 × 2.1 |
| Gradient: | Grad ACN + 0.1% FA:water + 0.1% FA (Formic Acid) 5:95(0 min) to 95:5(2.5 min) to 95:5(3 min) |
| Flow | 1.3 mL/min |

| Method G: | |
|---|---|
| Stationary phase: | Col Waters XBridge 4 |
| Gradient: | Grad water + 0.1% FA:ACN + 0.08% FA (Formic Acid) 97:3(0 min) to 40:60(3.5 min) to 2:98(5 min) |
| Flow | 1.3 mL/min |

(4-Bromo-benzyl)-(2,2-dimethoxy-ethyl)-amine (1)

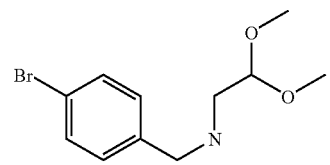

50 g (270.2 mmol) 4-bromobenzaldehyde were dissolved in 200 ml toluene and 28.4 g (270.2 mmol) aminoacetaldehyde dimethylacetal were added. After the addition of 5.1 g (27.0 mmol) p-toluenesulfonic acid monohydrate, the reaction mixture was heated under reflux in a Dean Stark apparatus. After 4 h, the reaction was cooled to room temperature and washed with saturated $NaHCO_3$-solution (2×) and $H_2O$. The combined aqueous layers were extracted with toluene and the combined organic layers were dried with $MgSO_4$ and evaporated. The residue was dissolved in 200 ml ethanol and 5.11 g (135.1 mmol) sodium borohydride were added in small portions. After stirring for 2 h at room temperature and standing overnight, 5.0 ml acetic acid were added and the solvent was removed i. vac. The residue was taken up in dichloromethane and washed (2×) with $H_2O$. After drying with $MgSO_4$ and evaporation, 60.5 g of the title compound were obtained, which were used without further purification. $R_t$=0.80 min (Method C). Detected mass: 274.1/276.1 $(M+H^+)$.

N-(4-Bromo-benzyl)-N-(2,2-dimethoxy-ethyl)-4-methyl-benzenesulfonamide (2)

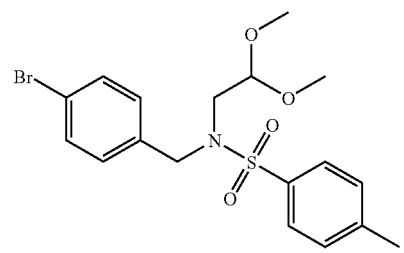 [SMILES: COC(CN(Cc1ccc(Br)cc1)S(=O)(=O)c1ccc(C)cc1)OC]

60.5 g (4-bromo-benzyl)-(2,2-dimethoxy-ethyl)-amine (1, crude product) were dissolved in 270 ml dichloromethane/pyridine (8:1). At 0° C. a solution of 76.0 g (386.4 mmol) p-toluenesulfonylchloride in 100 ml dichloromethane were added and the solution was stirred at room temperature. After 3 h, the reaction mixture was washed twice with 2 N HCl and saturated NaHCO$_3$-solution. The organic layer was dried with MgSO$_4$ and evaporated. Final silicagel chromatography (heptane/ethyl acetate 4:1) gave 59.9 g of the title compound. R$_t$=1.82 min (Method C). Detected mass: 396.1/398.1 (M-OMe$^-$).

6-Bromo-isoquinoline (3)

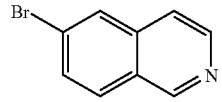 [SMILES: Brc1ccc2cnccc2c1]

To a mechanically stirred suspension of 95.2 g (699.5 mmol) AlCl$_3$ in 400 ml dichloromethane a solution of 59.9 g (139.8 mmol) N-(4-Bromo-benzyl)-N-(2,2-dimethoxy-ethyl)-4-methyl-benzenesulfonamide (2) in 400 ml dichloromethane was added and the reaction was stirred at room temperature for 4 h. After standing overnight, the reaction mixture was poured on ice, the organic layer was separated and the aqueous layer was extracted twice with dichloromethane. The combined dichloromethane solutions were washed with 1 N NaOH (2×) and saturated NaHCO$_3$-solution (2×). After drying with MgSO$_4$ and evaporation of the solvent, the crude product was purified by silicagel chromatography (heptane/ethyl acetate 1:1) to yield 17.5 g of the title compound. R$_t$=0.68 min (Method C). Detected mass: 208.1/210.1 (M+H$^+$).

(2R,4R)-4-(Isoquinolin-6-yloxy)-piperidine-1,2-dicarboxylic acid 1-tert-butyl ester 2-methyl ester (4)

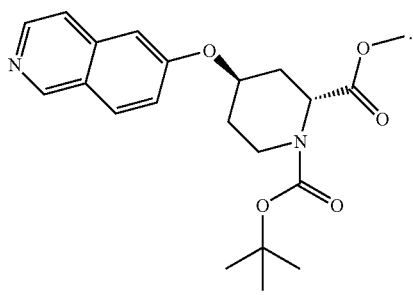 [SMILES: COC(=O)[C@H]1C[C@H](Oc2ccc3cnccc3c2)CCN1C(=O)OC(C)(C)C]

145 mg of 6-Hydroxisoquinoline and 311 mg of (2R,4S)-4-Hydroxy-piperidine-1,2-dicarboxylic acid 1-tert-butyl ester 2-methyl ester and 341 mg of triphenylphosphine were suspended in 3.5 ml of THF and 171 µl DIPEA were added. At 0° C. 261 mg DEAD were added slowly and the mixture was allowed to come to room temperature and stirred until no further increase in product could be monitored. After Evaporation the mixture was subjected to chromatography on silica gel (50 to 80% ethylacetate in Heptane) to give (2R,4R)-4-(Isoquinolin-6-yloxy)-piperidine-1,2-dicarboxylic acid 1-tert-butyl ester 2-methyl ester as an colorless oil.

(2R,4R)-4-(Isoquinolin-6-yloxy)-piperidine-1,2-dicarboxylic acid 1-tert-butyl ester (5)

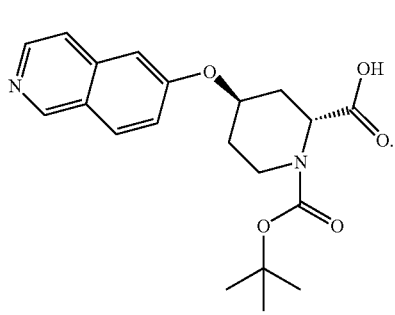 [SMILES: CC(C)(C)OC(=O)N1CC[C@@H](Oc2ccc3cnccc3c2)C[C@@H]1C(=O)O]

6.9 g crude (2R,4R)-4-(Isoquinolin-6-yloxy)-piperidine-1,2-dicarboxylic acid 1-tert-butyl ester 2-methyl ester (4) in 100 ml of methanol were treated with 10 ml of 2 N NaOH and stirred over night. After Evaporation the mixture was subjected to preparative HPLC. Lyophilisation gave (2R,4R)-4-(Isoquinolin-6-yloxy)-piperidine-1,2-dicarboxylic acid 1-tert-butyl ester as the trifluoroacetate as a white solid.

(2S,4S)-4-(Isoquinolin-6-yloxy)-piperidine-1,2-dicarboxylic acid 1-tert-butyl ester (6)

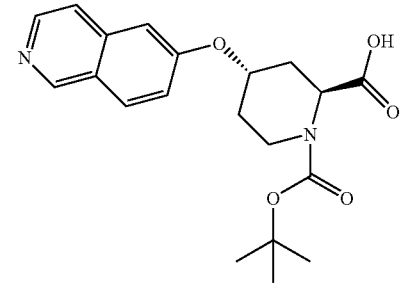 [SMILES: CC(C)(C)OC(=O)N1CC[C@H](Oc2ccc3cnccc3c2)C[C@H]1C(=O)O]

Starting from 6-Hydroxisoquinoline and (2S,4R)-4-Hydroxy-piperidine-1,2-dicarboxylic acid 1-tert-butyl ester 2-methyl ester (2S,4S)-4-(Isoquinolin-6-yloxy)-piperidine- 1,2-dicarboxylic acid 1-tert-butyl ester could be obtained as the trifluoroacetate, using a similar method as described for the synthesis of (5).

(2S,4R)-4-(Isoquinolin-6-yloxy)-pyrrolidine-1,2-dicarboxylic acid 1-tert-butyl ester (7)

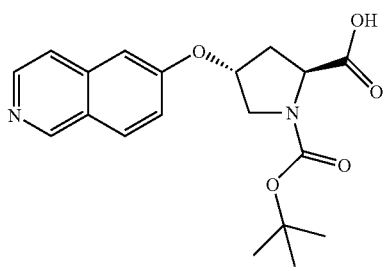 [SMILES: CC(C)(C)OC(=O)N1C[C@H](Oc2ccc3cnccc3c2)C[C@H]1C(=O)O]

Starting from 6-Hydroxisoquinoline and (2R,4S)-4-Hydroxy-pyrrolidine-1,2-dicarboxylic acid 1-tert-butyl ester 2-methyl ester (2S,4R)-4-(Isoquinolin-6-yloxy)-pyrrolidine-1,2-dicarboxylic acid 1-tert-butyl ester could be obtained as the trifluoroacetate.

(2R,4R)-4-(Isoquinolin-6-yloxy)-2-o-tolylcarbamoyl-piperidine-1-carboxylic acid tert-butyl ester (8)

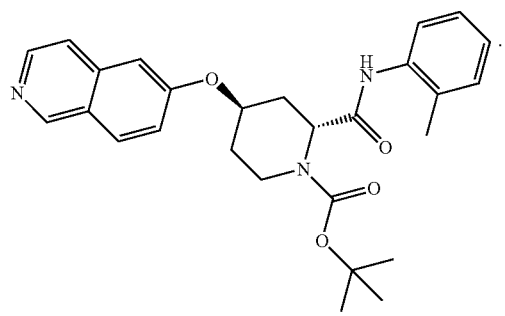 [SMILES: Cc1ccccc1NC(=O)[C@H]1C[C@H](Oc2ccc3cnccc3c2)CCN1C(=O)OC(C)(C)C]

28 mg 2-Methylaniline und 98 mg (2R,4R)-4-(Isoquinolin-6-yloxy)-piperidine-1,2-dicarboxylic acid 1-tert-butyl ester trifluoroacetate (5) were dissolved in 0.5 ml of DMF. 32 mg HOBT and 88.0 µl N-methylmorpholine were added follow by 44 mg EDC (free base) in 2 mol of dichloromethane. After stirring over night all volatiles were removed and the mixture subjected to preparative HPLC. Lyophilisation gave (2R,4R)-4-(Isoquinolin-6-yloxy)-2-o-tolylcarbamoyl-piperidine-1-carboxylic acid tert-butyl ester as the trifluoroacetate.

(2R,4R)-4-(Isoquinolin-6-yloxy)-piperidine-2-carboxylic acid o-tolylamide (9)

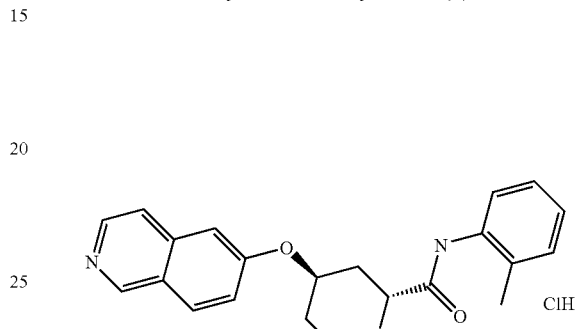

(2R,4R)-4-(Isoquinolin-6-yloxy)-2-o-tolylcarbamoyl-piperidine-1-carboxylic acid tert-butyl ester trifluoroacetate (8) was dissolved in 4 N HCl in dioxane and stirred for 2 h at rt. Evaporation gave (2R,4R)-4-(Isoquinolin-6-yloxy)-piperidine-2-carboxylic acid o-tolylamide as the hydrochloride. $R_t$=0.77 min (Method B). Detected mass: 362.2 (M+H$^+$).

The compounds described in the following table were obtained in a similar fashion as described for compound 8 and 9 respectively. All compounds were measured using method A (Table 1).

TABLE 1

| Cmpd. No. | Chemical Name | Amine | Product | Rt [min] | Mass [M + H$^+$] |
|---|---|---|---|---|---|
| 10 | (2R,4R)-4-(Isoquinolin-6-yloxy)-piperidine-2-carboxylic acid isobutyl-amide | H$_2$N-iBu | | 0.74 | 328.2 |
| 11 | (2R,4R)-4-(Isoquinolin-6-yloxy)-piperidine-2-carboxylic acid 3-methoxy-benzylamide | H$_2$N-CH$_2$-(3-methoxyphenyl) | | 0.79 | 392.2 |

TABLE 1-continued

| Cmpd. No. | Chemical Name | Amine | Product | Rt [min] | Mass [M + H+] |
|---|---|---|---|---|---|
| 12 | (2R,4R)-4-(Isoquinolin-6-yloxy)-piperidine-2-carboxylic acid 3-chloro-benzylamide | | | 0.87 | 396.2 |
| 13 | (2R,4R)-4-(Isoquinolin-6-yloxy)-piperidine-2-carboxylic acid phenethyl-amide | | | 0.84 | 376.2 |
| 14 | (2R,4R)-4-(Isoquinolin-6-yloxy)-piperidine-2-carboxylic acid (3-methoxy-propyl)-amide | | | 0.48 | 344.3 |
| 15 | (2R,4R)-4-(Isoquinolin-6-yloxy)-piperidine-2-carboxylic acid (2-hydroxy-ethyl)-amide | | | 0.16 | 316.3 |
| 16 | (2R,4R)-4-(Isoquinolin-6-yloxy)-piperidine-2-carboxylic acid (furan-2-ylmethyl)-amide | | | 0.64 | 352.3 |
| 17 | (2S,4S)-4-(Isoquinolin-6-yloxy)-piperidine-2-carboxylic acid (furan-2-ylmethyl)-amide | | | 0.57 | 352.2 |
| 18 | (2S,4S)-4-(Isoquinolin-6-yloxy)-piperidine-2-carboxylic acid (3-methoxy-propyl)-amide | | | 0.49 | 344.3 |
| 19 | (2S,4S)-4-(Isoquinolin-6-yloxy)-piperidine-2-carboxylic acid (pyridin-2-ylmethyl)-amide | | | 0.42 | 363.2 |
| 20 | (2S,4S)-4-(Isoquinolin-6-yloxy)-piperidine-2-carboxylic acid prop-2-ynylamide | | | 0.42 | 310.2 |

TABLE 1-continued

| Cmpd. No. | Chemical Name | Amine | Product | Rt [min] | Mass [M + H⁺] |
|---|---|---|---|---|---|
| 21 | (2S,4S)-4-(Isoquinolin-6-yloxy)-piperidine-2-carboxylic acid phenethyl-amide | | | 0.84 | 376.3 |
| 22 | (2S,4S)-4-(Isoquinolin-6-yloxy)-piperidine-2-carboxylic acid 2-chloro-benzylamide | | | 0.87 | 396.2 |
| 23 | (2S,4S)-4-(Isoquinolin-6-yloxy)-piperidine-2-carboxylic acid isobutyl-amide | | | 0.74 | 328.3 |
| 24 | (2S,4R)-4-(Isoquinolin-6-yloxy)-pyrrolidine-2-carboxylic acid (4-ethyl-phenyl)-amide | | | 1.01 | 362.2 |
| 25 | (2S,4R)-4-(Isoquinolin-6-yloxy)-pyrrolidine-2-carboxylic acid ((R)-1-phenyl-ethyl)-amide | | | 0.81 | 362.2 |
| 26 | (2S,4R)-4-(Isoquinolin-6-yloxy)-pyrrolidine-2-carboxylic acid (furan-2-ylmethyl)-amide | | | 0.58 | 338.2 |
| 27 | (2S,4R)-4-(Isoquinolin-6-yloxy)-pyrrolidine-2-carboxylic acid (2-hydroxy-ethyl)-amide | | | 0.17 | 302.2 |
| 28 | (2S,4R)-4-(Isoquinolin-6-yloxy)-pyrrolidine-2-carboxylic acid (2-methoxy-ethyl)-amide | | | 0.39 | 316.2 |
| 29 | (2S,4R)-4-(Isoquinolin-6-yloxy)-pyrrolidine-2-carboxylic acid (3-methoxy-propyl)-amide | | | 0.44 | 330.2 |

TABLE 1-continued

| Cmpd. No. | Chemical Name | Amine | Product | Rt [min] | Mass [M + H+] |
|---|---|---|---|---|---|
| 30 | (2S,4R)-4-(Isoquinolin-6-yloxy)-pyrrolidine-2-carboxylic acid (pyridin-2-ylmethyl)-amide | | | 0.21 | 349.2 |
| 31 | (2S,4R)-4-(Isoquinolin-6-yloxy)-pyrrolidine-2-carboxylic acid prop-2-ynylamide | | | 0.40 | 296.2 |

(2S,4R)-4-(Isoquinolin-6-ylamino)-pyrrolidine-1,2-dicarboxylic acid 1-tert-butyl ester 2-methyl ester (32)

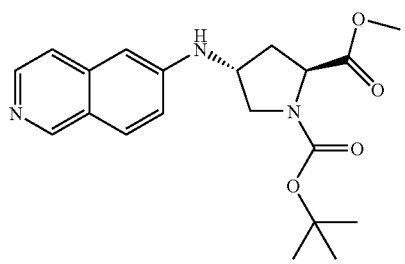 [SMILES: COC(=O)[C@@H]1C[C@@H](Nc2ccc3cnccc3c2)CN1C(=O)OC(C)(C)C]

124 mg of 6-bromoisoquinoline (3), 488 mg of cesium carbonate and 202 mg (2S,4R)-4-amino-pyrrolidine-1,2-dicarboxylic acid 1-tert-butyl ester 2-methyl ester hydrochloride were dissolved in 6 ml of DMF and degassed. 46 mg Palladium acetate and 132 mg of Xanthphos were added and the mixture was stirred at 100° C. for 5 h. After cooling to rt the mixture was filtrated, evaporated and the residue was purified by chromatography on silica gel (50% ethyl acetate in heptane to 100% ethyl acetate). To obtain (2S,4R)-4-(Isoquinolin-6-ylamino)-pyrrolidine-1,2-dicarboxylic acid 1-tert-butyl ester 2-methyl ester as a colourless oil.

(2S,4R)-4-(Isoquinolin-6-ylamino)-pyrrolidine-1,2-dicarboxylic acid 1-tert-butyl ester (33)

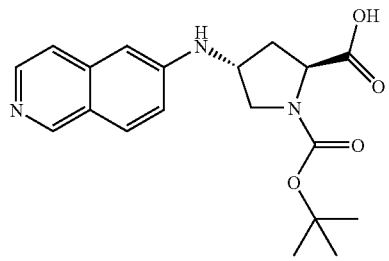 [SMILES: CC(C)(C)OC(=O)N1C[C@H](Nc2ccc3cnccc3c2)C[C@H]1C(=O)O]

1.4 g of (2S,4R)-4-(Isoquinolin-6-ylamino)-pyrrolidine-1,2-dicarboxylic acid 1-tert-butyl ester 2-methyl ester (32) were dissolved in 15 ml of methanol and treated with 3.4 ml of 2 N NaOH at rt until saponification was complete. After evaporation the residue was subjected to preparative HPLC and lyophilized to obtain (2S,4R)-4-(Isoquinolin-6-ylamino)-pyrrolidine-1,2-dicarboxylic acid 1-tert-butyl ester as the trifluoroacetate.

(2S,4R)-2-(4-Ethyl-phenylcarbamoyl)-4-(isoquinolin-6-ylamino)-pyrrolidine-1-carboxylic acid tert-butyl ester (34)

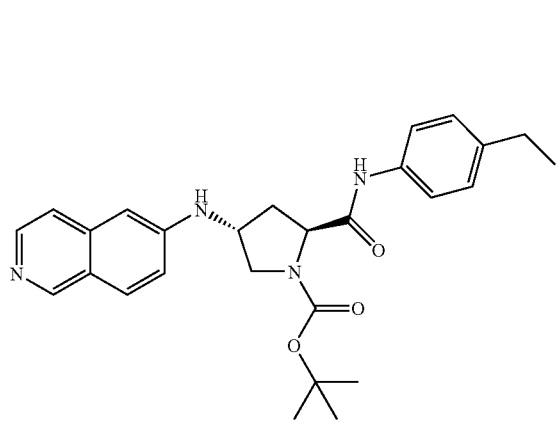 [SMILES: CCc1ccc(NC(=O)[C@@H]2C[C@@H](Nc3ccc4cnccc4c3)CN2C(=O)OC(C)(C)C)cc1]

94 mg (2S,4R)-4-(Isoquinolin-6-ylamino)-pyrrolidine-1,2-dicarboxylic acid 1-tert-butyl ester (33) and 32 mg 4-ethylaniline were dissolved in 0.5 ml DMF and a solution of 33 mg HOAT in 0.5 ml DMF and 100 µl DIPEA were added, followed by 112 mg PyBroP in 2 ml dichloromethane. After stirring over night all volatiles were evaporated and the mixture purified by preparative HPLC to obtain (2S,4R)-2-(4- ethyl-phenylcarbamoyl)-4-(isoquinolin-6-ylamino)-pyrrolidine-1-carboxylic acid tert-butyl ester as the trifluoroacetate salt.

(2S,4R)-4-(Isoquinolin-6-ylamino)-pyrrolidine-2-carboxylic acid (4-ethyl-phenyl)-amide (35)

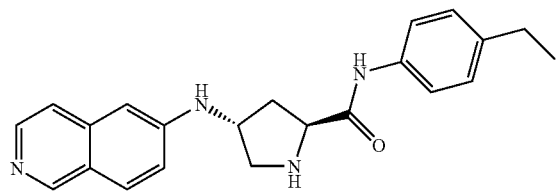 [SMILES: CCc1ccc(NC(=O)[C@@H]2C[C@@H](Nc3ccc4cnccc4c3)CN2)cc1]

(2S,4R)-2-(4-Ethyl-phenylcarbamoyl)-4-(isoquinolin-6-ylamino)-pyrrolidine-1-carboxylic acid tert-butyl ester trifluoroacetate was dissolved in 4 N HCl in dioxane and stirred for 2 h at rt. Evaporation gave (2S,4R)-4-(Isoquinolin-6-ylamino)-pyrrolidine-2-carboxylic acid (4-ethyl-phenyl)-amide as the hydrochloride salt. $R_t$=1.05 min (Method A). Detected mass: 361.2 (M+H$^+$).

(2S,4S)-4-(Isoquinolin-6-ylamino)-pyrrolidine-1,2-dicarboxylic acid 1-tert-butyl ester (36)

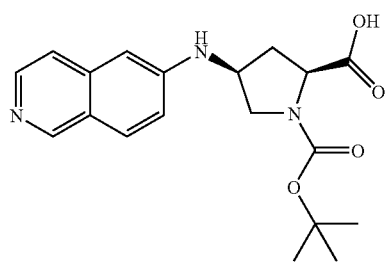 [SMILES: CC(C)(C)OC(=O)N1C[C@@H](Nc2ccc3cnccc3c2)C[C@H]1C(=O)O]

In analogy to the preparation of (33), (2S,4S)-4-(Isoquinolin-6-ylamino)-pyrrolidine-1,2-dicarboxylic acid 1-tert-butyl ester was prepared as the trifluoracetate from 6-bromoisoquinoline (3) and (2S,4S)-4-Amino-pyrrolidine-1,2-dicarboxylic acid 1-tert-butyl ester 2-methyl ester hydrochloride.

(3S,4R)-4-(Isoquinolin-6-ylamino)-pyrrolidine-1,3-dicarboxylic acid 1-tert-butyl ester (37)

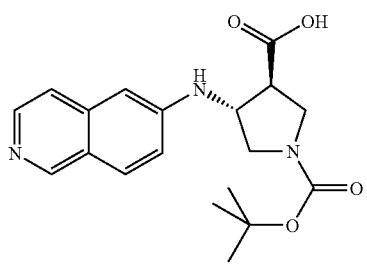 [SMILES: CC(C)(C)OC(=O)N1C[C@H](Nc2ccc3cnccc3c2)[C@@H](C(=O)O)C1]

In analogy to the preparation of (33), (3S,4R)-4-(Isoquinolin-6-ylamino)-pyrrolidine-1,3-dicarboxylic acid 1-tert-butyl ester was prepared as the trifluoracetate from 6-Bromisoquinoline and (3S,4R)-4-Amino-pyrrolidine-1,3-dicarboxylic acid 1-tert-butyl ester 3-methyl ester The compounds described in the following table 2 were obtained in a similar fashion as described for compound 34 and 35. All compounds were measured using method A.

TABLE 2

| Compound No. | Chemical Name | Amine | Product | Rt [min] | Mass [M + H$^+$] |
|---|---|---|---|---|---|
| 38 | (2S,4R)-4-(Isoquinolin-6-ylamino)-pyrrolidine-2-carboxylic acid (furan-2-ylmethyl)-amide | H$_2$N-CH$_2$-furan | (structure) | 0.67 | 337.2 |
| 39 | (2S,4R)-4-(Isoquinolin-6-ylamino)-pyrrolidine-2-carboxylic acid (2-methoxy-ethyl)-amide | H$_2$N-CH$_2$CH$_2$-O-CH$_3$ | (structure) | 0.46 | 315.2 |
| 40 | (2S,4R)-4-(Isoquinolin-6-ylamino)-pyrrolidine-2-carboxylic acid (3-methoxy-propyl)-amide | H$_2$N-(CH$_2$)$_3$-O-CH$_3$ | (structure) | 0.60 | 329.3 |

TABLE 2-continued

| Compound No. | Chemical Name | Amine | Product | Rt [min] | Mass [M + H+] |
|---|---|---|---|---|---|
| 41 | (2S,4S)-4-(Isoquinolin-6-ylamino)-pyrrolidine-2-carboxylic acid (furan-2-ylmethyl)-amide | | | 0.60 | 337.2 |
| 42 | (2S,4S)-4-(Isoquinolin-6-ylamino)-pyrrolidine-2-carboxylic acid (3-methoxy-propyl)-amide | | | 0.55 | 329.2 |
| 43 | (2S,4S)-4-(Isoquinolin-6-ylamino)-pyrrolidine-2-carboxylic acid (pyridin-2-ylmethyl)-amide | | | 0.16 | 348.2 |
| 44 | (2S,4S)-4-(Isoquinolin-6-ylamino)-pyrrolidine-2-carboxylic acid (4-ethyl-phenyl)-amide | | | 0.96 | 361.3 |
| 45 | (2S,4S)-4-(Isoquinolin-6-ylamino)-pyrrolidine-2-carboxylic acid phenethyl-amide | | | 0.82 | 361.3 |
| 46 | (2S,4S)-4-(Isoquinolin-6-ylamino)-pyrrolidine-2-carboxylic acid 2-chloro-benzylamide | | | 0.84 | 381.2 |
| 47 | (2S,4S)-4-(Isoquinolin-6-ylamino)-pyrrolidine-2-carboxylic acid isobutyl-amide | | | 0.67 | 313.3 |
| 48 | (3S,4R)-4-(Isoquinolin-6-ylamino)-pyrrolidine-3-carboxylic acid 3-methoxy-benzylamide | | | 0.83 | 377.2 |

TABLE 2-continued

| Compound No. | Chemical Name | Amine | Product | Rt [min] | Mass [M + H⁺] |
|---|---|---|---|---|---|
| 49 | (3S,4R)-4-(Isoquinolin-6-ylamino)-pyrrolidine-3-carboxylic acid (2-methoxy-ethyl)-amide | H₂N—⟨⟩—O—⟨⟩ | [structure] | 0.68 | 315.1 |
| 50 | (3S,4R)-4-(Isoquinolin-6-ylamino)-pyrrolidine-3-carboxylic acid o-tolylamide | H₂N—⟨Ar⟩ | [structure] | 0.86 | 347.1 |
| 51 | (3S,4R)-4-(Isoquinolin-6-ylamino)-pyrrolidine-3-carboxylic acid isobutyl-amide | H₂N—⟨⟩ | [structure] | 0.75 | 313.2 |

6-(8-Methyl-8-aza-bicyclo[3.2.1]oct-3-yloxy)-isoquinoline (52)

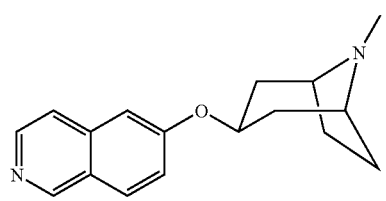 [SMILES: CN1C2CCC1CC(Oc1ccc3cnccc3c1)C2]

6-(8-Methyl-8-aza-bicyclo[3.2.1]oct-3-yloxy)-2H-isoquinolin-1-one (53)

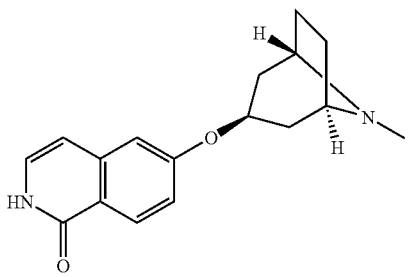 [SMILES: CN1[C@@H]2CC[C@H]1C[C@H](Oc1ccc3c(=O)[nH]ccc3c1)C2]

625 mg of triphenyl phosphine were dissolved in 20 mL of dry dichloromethane, 0.095 mL of diethyl azodicarboxylate were added and the solution was shaken for 20 minutes. 69 μL of triethyl amine, 72.6 mg of 6-hydroxy isoquinoline and 67.1 mg of tropine were added and the mixture was shaken overnight. The reaction mixture was filtered, the remainders washed thoroughly with dichloromethane and the combined organic layer was extracted twice with 1N sodium hydroxide and water, respectively. The organic layer was dried, evaporated to dryness and the crude material was purified by HPLC. The product was dissolved in 2N HCl and lyophilized to give 23 mg of 6-(8-Methyl-8-aza-bicyclo[3.2.1]oct-3-yloxy)-isoquinoline (52) as the hydrochloride. $R_t$=0.52 min (Method A). Detected mass: 269.2 (M+H⁺).

8 mL of dry dichloromethane were added to 814 mg (1.73 mmol) of polystyrene bound triphenyl phosphine. At 0° C. 234 μL (1.48 mmol) of diethyl azodicarboxylate were added. 200 mg (1.24 mmol) of 6-hydroxy-2H-isoquinolinone (66), 210 mg (1.49 mmol) of tropine and 261 μL of triethylamine were added and the reaction mixture was allowed to warm to room temperature and stirred overnight. Another 279 mg of PS-triphenyl phosphine, 43 mg of tropine, 26 μL of diethyl azodicarboxylate and 2 mL of dry dichloeomethane were added and stirring was continued overnight. The solids were filtered off and washed with THF. The mixture was evaporated and purified by flash chromatography to give 158 mg of 6-(8-methyl-8-aza-bicyclo[3.2.1]oct-3-yloxy)-2H-isoquinolin-1-one (53). $R_t$=0.79 min (Method B). Detected mass: 279.2 (M+H$^+$).

3-Chloro-4-fluoro-benzyl)-(2,2-dimethoxy-ethyl)-amine (54)

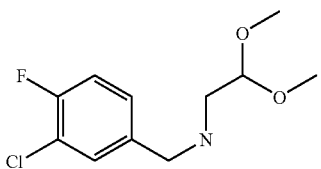 [SMILES: COC(CNCc1ccc(F)c(Cl)c1)OC]

100 g (0.63 mol) of 3-chloro-4-fluoro-benzaldehyde were dissolved in 300 ml of toluene and 66.3 g (0.63 mol) of aminoacetaldehyde-dimethylacetal were added at room temperature. After adding 12.0 g (0.06 mol) of p-toluenesulfonic acid monohydrate, the reaction was heated in a Dean-Stark apparatus for 3 h. The solution was than cooled to room temperature and washed twice with saturated NaHCO$_3$-solution and water. The aqueous solutions were extracted with toluene. The combined organic layers were dried with MgSO$_4$ and evaporated. The obtained imine-intermediate was dissolved directly in 300 mL of ethanol and 11.93 g (0.32 mol) of sodium borohydride were added in small portions. After stirring overnight, 10 mL of acetic acid were added and the solvent was removed i. vac. The residue was dissolved in dichloromethane and washed twice with water. After drying with MgSO$_4$ and evaporation of the solvent, 147.0 g of crude product were obtained as a yellow oil, which was used without further purification. $R_t$=0.81 min (Method C). Detected mass: 248.2 (M+H$^+$).

N-(3-Chloro-4-fluoro-benzyl)-N-(2,2-dimethoxy-ethyl)-4-methyl-benzene-sulfonamide (55)

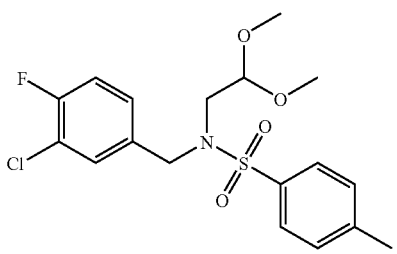 [SMILES: COC(CN(Cc1ccc(F)c(Cl)c1)S(=O)(=O)c1ccc(C)cc1)OC]

147.0 g (3-Chloro-4-fluoro-benzyl)-(2,2-dimethoxy-ethyl)-amine (54, crude product) were dissolved in 540 ml of dichloromethane/pyridine (8:1). At 0° C. a solution of 145.8 g (1.04 mol) p-toluenesulfonylchloride in 200 ml of dichloromethane was added. After 5 h at room temperature additional 20 ml of pyridine, 29.16 g (0.15 mol) p-toluene-sulfonylchloride and a catalytic amount of DMAP were added. The solution was stirred at room temperature for 7 h and then refluxed for additional 4 h. Again 29.16 g (0.15 mol) p-toluene-sulfonylchloride and a catalytic amount of DMAP were added and the mixture was stirred overnight. For workup, the solution was washed twice with 2 N HCl and twice with saturated NaHCO$_3$-solution. The organic layer was dried with MgSO$_4$ and evaporated. Final silicagel chromatography (heptane/ethyl acetate 4:1) gave 155 g of the title compound as a yellow oil. $R_t$=1.80 min (Method B). Detected mass: 370.2 (M-OMe$^-$).

7-Chloro-6-fluoro-isoquinoline (56)

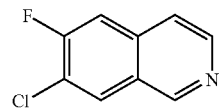

343.6 (2.54 mol) of AlCl$_3$ were suspended in 1.1 l of dichloromethane and were stirred for 30 min with a mechanical stirrer. To this suspension, a solution of 204 g (0.51 mol) (N-(3-chloro-4-fluoro-benzyl)-N-(2,2-dimethoxy-ethyl)-4-methyl-benzene-sulfonamide (55) was added and the mixture was stirred at room temperature for 5 h. After standing overnight, the reaction suspension was poured on ice, the organic layer was separated and the aqueous phase was extracted twice with dichloromethane. The combined organic layers were washed twice with 1 N NaOH and saturated NaHCO$_3$-solution, dried with MgSO$_4$ and evaporated. The obtained crude product was purified by silicagel chromatography (heptane/ethyl acetate 1:1), which gave 61.3 g of the title compound. $R_t$=0.73 min (Method B). Detected mass: 182.1 (M+H$^+$).

7-Chloro-6-fluoro-isoquinoline 2-oxide (57)

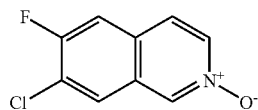 [SMILES: [O-][n+]1ccc2cc(F)c(Cl)cc2c1]

25 g (137.7 mmol) of 7-Chloro-6-fluoro-isoquinoline (56) were in dissolved in 500 ml of dichloromethane. At room temperature 50.9 g (206.5 mmol) of 3-chloro-peroxy benzoic acid (70%) were added and the mixture was stirred at room temperature until complete conversion was achieved. For workup, the precipitate was filtered off and washed with dichloromethane. The filtrate was washed twice with NaHCO$_3$-solution. The layers were separated and the aqueous phase was extracted twice with dichloromethane. The organic phases were dried with MgSO$_4$ and evaporated. The so obtained solid material (18.4 g) was used without further purification. $R_t$=0.87 min (Method C). Detected mass: 198.1/200.1 (M+H$^+$).

6-Methoxy-isoquinoline 2-oxide (58)

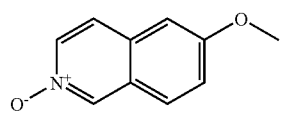

Starting from 4-methoxy-benzaldehyde, 6-methoxy-isoquinoline 2-oxide (58) was prepared following a similar route as described for 7-chloro-6-fluoro-isoquinoline 2-oxide (57). $R_t$=0.70 min (Method C). Detected mass: 176.1 (M+H$^+$).

1,7-Dichloro-6-fluoro-isoquinoline (59)

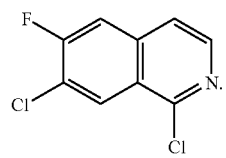

2.6 g (12.0 mmol) of 7-Chloro-6-fluoro-isoquinoline 2-oxide (57) were heated in 40 ml of POCl$_3$ at reflux for 4 h. After the mixture has cooled down to room temperature, it was poured on ice. The aqueous solution was extracted three times with dichloromethane. The combined organic layers were dried with MgSO$_4$ and evaporated to yield 2.91 g of the title compound, which was used without further purification. $R_t$=2.34 min (Method A). Detected mass: 216.0/218.0 (M+H$^+$).

7-Chloro-6-fluoro-2H-isoquinolin-1-one (60)

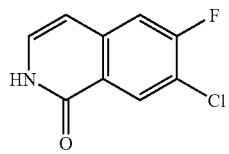 [SMILES: O=c1[nH]ccc2cc(F)c(Cl)cc12]

41.1 g 1,7-dichloro-6-fluoro-isoquinoline (59) were dissolved in 670 ml of acetic acid. After addition of 148.8 g of ammonium acetate, the solution was stirred at 100° C. After 3 h, the solvent was removed under reduced pressure and the residue was poured into water. The aqueous phase was extracted three times with dichloromethane, the combined organic layer was washed with saturated sodium bicarbonate solution and brine, dried over sodium sulfate and evaporated to dryness. The crude product was crystallized from ethyl acetate:heptane to yield 14.85 g of the desired product. Another 4.5 g could be obtained upon evaporation and silica gel chromatography of the mother liquor. The precipitate was filtered and dried to yield 9.91 g (83%) of the title compound. $R_t$=1.33 min (Method B). Detected mass: 198.0 (M+H$^+$).

1-Benzyloxy-7-chloro-6-fluoro-isoquinoline (61)

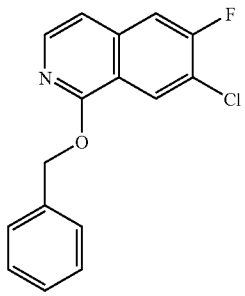 [SMILES: Fc1cc2ccnc(OCc3ccccc3)c2cc1Cl]

14.74 g (74.6 mmol) of 7-chloro-6-fluoro-2H-isoquinolin-1-one (60) were dissolved in 150 ml of toluene. After addition of 30.86 g (111.9 mmol) of silver carbonate and 15.31 g (89.5 mmol) of benzyl bromide, the mixture was stirred at 80° C. for 3 h. After cooling down to room temperature, the reaction mixture was filtered and the filtrate was evaporated. The residue was dissolved in dichloromethane and washed with water, dried with magnesium sulfate and evaporated. Final purification by MPLC gave 11.63 g of the title compound. $R_t$=2.51 min (Method B). Detected mass: 288.1/290.1 (M+H$^+$).

7-Chloro-6-fluoro-2-(4-methoxy-benzyl)-2H-isoquinolin-1-one (62)

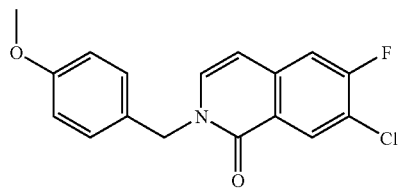 [SMILES: COc1ccc(Cn2ccc3cc(F)c(Cl)cc3c2=O)cc1]

10 g of 7-chloro-6-fluoro-2H-isoquinolin-1-one (60) were suspended in 100 mL of DMF. 19.75 g of cesium carbonate and 7.55 mL of p-methoxy benzyl chloride were added successively and the mixture was stirred for 2 h. The mixture was poured on ice/water and the formed precipitate was filtered off, washed with water and dried in vacuum to give 13.67 g of the title compound. $R_t$=1.96 min (Method B). Detected mass: 318.1 (M+H$^+$).

6-Fluoro-2-(4-methoxy-benzyl)-7-methyl-2H-isoquinolin-1-one (63)

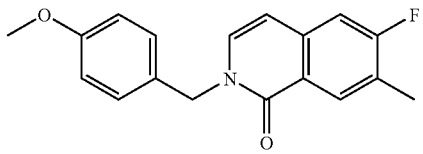 [SMILES: COc1ccc(Cn2ccc3cc(F)c(C)cc3c2=O)cc1]

Starting from 3-methyl-4-fluoro benzaldehyde, the title compound was prepared following a similar sequence as described for 7-chloro-6-fluoro-2-(4-methoxy-benzyl)-2H-isoquinolin-1-one (62). $R_t$=1.83 min (Method B). Detected mass: 298.1 (M+H$^+$).

6-Fluoro-2-(4-methoxy-benzyl)-2H-isoquinolin-1-one (64)

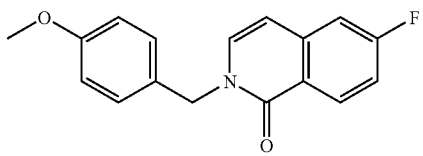 [SMILES: COc1ccc(Cn2ccc3cc(F)ccc3c2=O)cc1]

Starting from 4-fluoro benzaldehyde, the title compound was prepared following a similar sequence as described for 7-chloro-6-fluoro-2-(4-methoxy-benzyl)-2H-isoquinolin-1-one (62). $R_t$=1.72 min (Method B). Detected mass: 284.1 (M+H$^+$).

6-Methoxy-2H-isoquinolin-1-one (65)

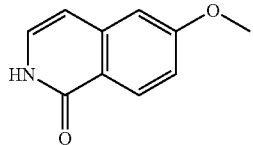

5.2 g of 6-Methoxy-isoquinoline 2-oxide (58) was heated in 120 mL of acetic anhydride at 100° C. for 3 h. The reaction mixture was evaporated and the residue was taken up in 2 M NaOH and heated at 100° C. for another hour. The mixture was allowed to cool down and the pH was adjusted by addition of 2N HCl to 6. The aqueous layer was extracted several times with methyl-tert.butyl ether, the combined organic layer was dried over sodium sulphate and evaporated. The crude material was purified by silica gel chromatography to yield 3.26 g of the desired product.

$R_t$=0.93 min (Method C). Detected mass: 176.1 (M+H$^+$).

6-Hydroxy-2H-isoquinolin-1-one (66)

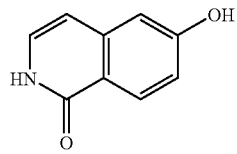 [SMILES: O=c1[nH]ccc2cc(O)ccc12]

2.54 g of 6-Methoxy-2H-isoquinolin-1-one (65) were dissolved in 50 mL of dry dichloromethane and at 0° C. 2.74 mL of boron tribromide were carefully added. The mixture was allowed to stir at room temperature for 18 h and was then poured on ice/water. The organic layer was separated, washed with brine, dried over sodium sulphate and evaporated to dryness. The crude material was purified by silica gel chromatography to yield 1.96 g of the desired product.

$R_t$=0.64 min (Method C). Detected mass: 162.2 (M+H$^+$).

1-Benzyl-4-phenyl-piperidin-4-ol (67)

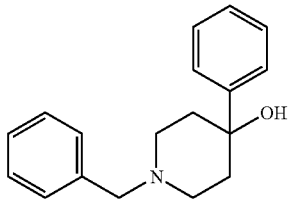 [SMILES: OC1(c2ccccc2)CCN(Cc2ccccc2)CC1]

A solution of phenylmagnesium chloride in THF (25%, 33 mL) was added at −10° C. to a solution of 1-Benzylpiperidone (10 g, dissolved in THF). The mixture was warmed to room temperature, stirred for 4 h and quenched by addition of 20% ammonium chloride solution. The mixture was extracted three times with methyl tert. butyl ether and the combined organic layer was dried over sodium sulfate and evaporated to dryness. The crude product was purified by silica gel chromatography to give 14.3 g of the desired product as an orange oil. $R_t$=1.09 min (Method B). Detected mass: 268.1 (M+H$^+$).

1-Benzyloxy-6-(1-benzyl-4-phenyl-piperidin-4-yloxy)-7-chloro-isoquinoline (68)

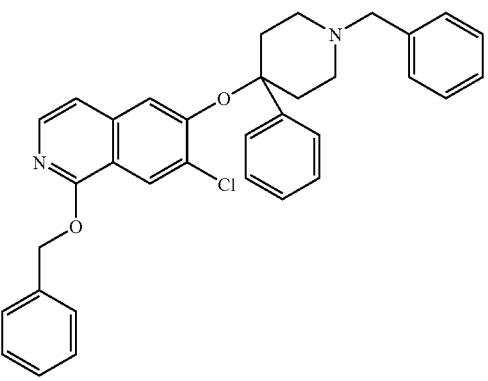 [SMILES: Clc1cc2c(OCc3ccccc3)nccc2cc1OC1(c2ccccc2)CCN(Cc2ccccc2)CC1]

566 mg of 1-Benzyl-4-phenyl-piperidin-4-ol (67) were dissolved in 6 ml of dry dimethyl acetamide. 48 mg of sodium hydride (95%) were added and after 1 h of stirring, 580 mg of 1-benzyloxy-7-chloro-6-fluoro-isoquinoline (61), dissolved in 6 ml of dry dimethyl acetamide were added. The course of the reaction was monitored by LCMS and 50 mg of sodium hydride were added several times until no further conversion could be observed. 10 mL of water were added. The resulting precipitate was purified by silica gel chromatography to give 930 mg of the desired product, sufficiently pure for further conversion. $R_t$=1.62 min (Method C). Detected mass: 536.2 (M+H$^+$).

6-(1-Benzyl-4-phenyl-piperidin-4-yl oxy)-7-chloro-2H-isoquinolin-1-one (69)

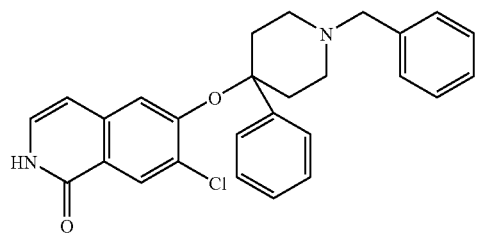 [SMILES: O=c1[nH]ccc2cc(OC3(c4ccccc4)CCN(Cc4ccccc4)CC3)c(Cl)cc12]

920 mg of 1-Benzyloxy-6-(1-benzyl-4-phenyl-piperidin-4-yloxy)-7-chloro-isoquinoline (68) were suspended in 1M HCl and dissolved by addition of methanol. After stirring overnight, the solution was diluted with water, extracted with methyl tert. butyl ether and the aqueous layer was lyophilized. The product was purified by crystallization to give 98 mg of the desired product as a white solid as the hydrochloride. $R_t$=1.46 min (Method A). Detected mass: 445.3 (M+H$^+$).

3-Hydroxy-8-aza-bicyclo[3.2.1]octane-8-carboxylic acid tert-butyl ester (70)

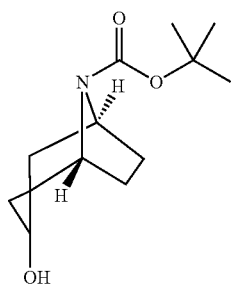 [SMILES: CC(C)(C)OC(=O)N1[C@H]2CC[C@@H]1C1(CC1O)C2]

To a 0° C. cold solution of 2.00 g N-Boc-nortropinone in 50 mL of methanol was added portionwise 672 mg of sodium borohydride. The reaction mixture was stirred at 0° C. for 1 h. The solvent was evaporated, the crude product was taken up in dichloromethane and treated with sat. sodium bicarbonate solution. The phases were separated and the aqueous phase extracted twice with dichloromethane. The organic phases were combined, dried over magnesium sulfate and concentrated to give 3-hydroxy-8-aza-bicyclo[3.2.1]octane-8-carboxylic acid tert-butyl ester (70) as diastereomeric mixture. $R_t$=1.11 min, 1.17 min (Method C). Detected mass: 128.0 (M-Boc+H$^+$).

3-[7-Chloro-2-(4-methoxy-benzyl)-1-oxo-1,2-dihydro-isoquinolin-6-yloxy]-8-aza-bicyclo[3.2.1]octane-8-carboxylic acid tert-butyl ester (71)

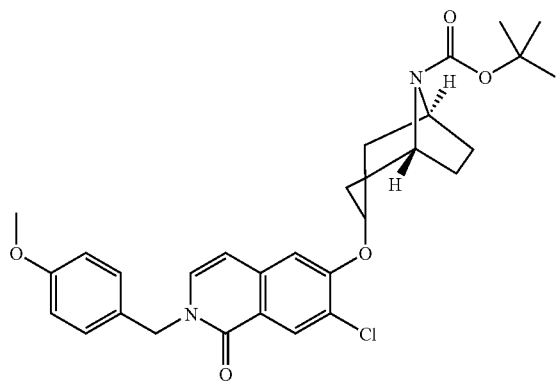 [SMILES: COc1ccc(Cn2ccc3cc(OC4CC45C[C@@H]4CC[C@H]5N4C(=O)OC(C)(C)C)c(Cl)cc3c2=O)cc1]

528 mg of sodium hydride (60%) were suspended in 8 mL of dimethyl acetamide and 1.00 g of 3-hydroxy-8-aza-bicyclo[3.2.1]octane-8-carboxylic acid tert-butyl ester (70), dissolved in 4 mL of dimethyl acetamide, were added dropwise. After 1 h, 1.40 g of 7-Chloro-6-fluoro-2-(4-methoxy-benzyl)-2H-isoquinolin-1-one (62), dissolved in another 8 mL of dimethyl acetamide, were added. The reaction mixture was stirred at room temperature until the reaction was complete. 30 mL of water were added, the resulting suspension extracted three times with a mixture of dichloromethane and 2-propanol (3:1) and the combined organic layers were evaporated. Water was added and the crude product was subjected to lyophilization to remove remainders of dimethyl acetamide. The obtained crude product was purified by silica gel chromatography to yield 1.85 g of the title compound as a mixture of diastereoisomers (71). $R_t$=1.95 min, 2.03 min (Method C). Detected mass: 525.0 (M+H$^+$).

6-(8-Aza-bicyclo[3.2.1]oct-3-yloxy)-7-chloro-2H-isoquinolin-1-one (72, 73)

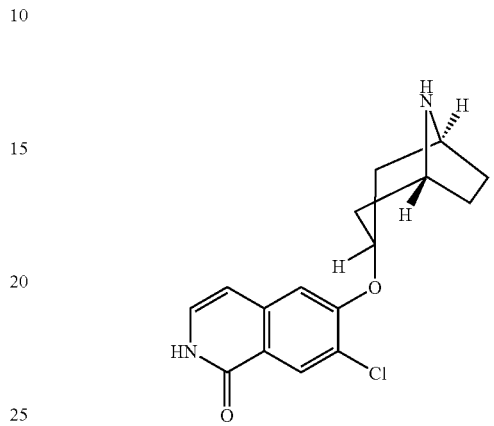

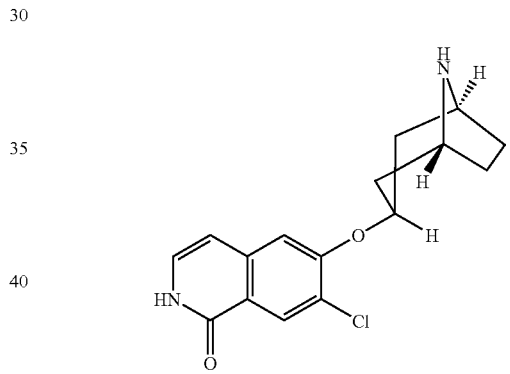

1.70 g of 3-[7-chloro-2-(4-methoxy-benzyl)-1-oxo-1,2-dihydro-isoquinolin-6-yloxy]-8-aza-bicyclo[3.2.1]octane-8-carboxylic acid tert-butyl ester (71) were dissolved in 6 mL of TFA and heated in a microwave oven at 150° C. for 1 h. Methanol was added and the reaction mixture was evaporated. The pure diastereomers were obtained as hydrochlorides by separation of the mixture via preparative HPLC and lyophilization of the residues from 2N HCl and water, respectively. Stereoisomer 1 (72): $R_t$=0.81 min (Method A). Detected mass: 305.2 (M+H$^+$). Stereoisomer 2 (73): $R_t$=0.88 min (Method A). Detected mass: 305.2 (M+H$^+$), 346.2 (M-NH$_3$+H$^+$).

The following products were synthesized in a similar fashion as described for the synthesis of 72/73 using the designated isoquinolinone starting material and tropinone as aminoalcohol component. HCl salts of the compounds could be obtained by taking up the evaporated crude product or chromatographed material in 1M HCl, washing of the aqueous phase with dichloromethane and subsequent lyophilization, followed by twice taking up in water and lyophilzation again, eventually followed by recrystallization from isopropanol

TABLE 3

| Compound No. | Chemical Name | Isoquinolinone | Product | $R_t$ [min] | Mass [M + H$^+$] | Method |
|---|---|---|---|---|---|---|
| 74 | 6-(8-Methyl-8-aza-bicyclo[3.2.1]oct-3-yloxy)-2H-isoquinolin-1-one | 64 | | 0.77 | 285.2 | B |
| 75 | 7-Chloro-6-(8-methyl-8-aza-bicyclo[3.2.1]oct-3-yloxy)-2H-isoquinolin-1-one | 62 | | 0.99 | 319.1 | B |
| 76 | 7-Methyl-6-(8-methyl-8-aza-bicyclo[3.2.1]oct-3-yloxy)-2H-isoquinolin-1-one | 63 | | 0.85 | 299.1 | B |

N6-(4-Amino-4-phenyl-cyclohexyl)-isoquinoline-1,6-diamine (77)

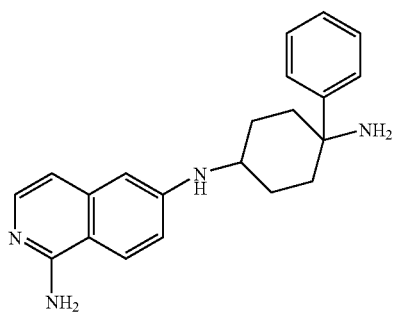 [SMILES: Nc1nccc2cc(NC3CCC(N)(c4ccccc4)CC3)ccc12]

100 mg (0.278 mmol) of (6-amino-isoquinolin-1-yl)-dicarbamic acid tert-butyl ester were dissolved in 0.5 ml of methanol. After addition of molecular sieves 4 Å, 56.3 mg (0.57 mmol) of triethyl amine, 167 mg (2.78 mmol) of acetic acid and 241 mg (0.835 mmol) of (4-oxo-1-phenyl-cyclohexyl)-carbamic acid tert-butyl ester were added, and the mixture was stirred for 1 h. Then a solution of 52.4 mg (0.835 mmol) of sodium cyano borohydride was added dropwise and the mixture was stirred at 70° C. until no further conversion was observed. The solution was filtered and the solvent was removed under reduced pressure. The residue was dissolved in dichloromethane, washed with 1 N NaOH and sat. sodium chloride solution, dried with magnesium sulfate and evaporated. The crude product was stirred in 4 N HCl/dioxane, evaporated, dissolved in water and freeze dried to yield 2.7 mg of the desired product as its hydrochloride. $R_t$=2.22 min (Method G). Detected mass: 333.3 (M+H$^+$).

Determination of Rho-Kinase Activity

To measure Rho-kinase inhibition, IC$_{50}$ values were determined according to the following protocol:

Active human recombinant ROCK II (N-terminal His6-tagged recombinant human ROCK-II residues 11-552) was purchased from Upstate Ltd., Dundee, UK. The peptide substrate, Fluorescein-AKRRRLSSLRA-COOH, was obtained from JPT Peptide Technologies, Berlin, Germany. Adenosine-5'-triphosphate (ATP), bovine serum albumine (BSA), dimethylsulphoxide (DMSO), 4-(2-Hydroxyethyl)piperazine-1-ethanesulfonic acid (Hepes), Brij-35 and dithiothreitol (DTT) were purchased from Sigma-Aldrich, Munich, Germany. Tris(hydroxymethyl)-aminomethane (Tris), magnesium chloride, NaOH, 1M HCl and EDTA were obtained from Merck Biosciences, Darmstadt, Germany. "Complete" protease inhibitor was from Roche Diagnostics, Mannheim, Germany.

Test compounds were diluted to the appropriate concentrations in buffer 1 (25 mM Tris-HCl, pH 7.4, 5 mM MgCl$_2$, 2 mM DTT, 0.02% (w/v) BSA and 3% DMSO). The ROCK II enzyme was diluted to a concentration of 100 ng/ml in buffer 2 (25 mM Tris-HCl, pH 7.4, 5 mM MgCl$_2$, 2 mM DTT and 0.02% (w/v) BSA). The peptide substrate and ATP were diluted to concentrations of 3 µM and 120 µM, respectively, in the buffer 2. Two µl of the compound solution were mixed with 2 µl of the diluted enzyme in a 384-well small volume microtiter plate (Greiner, Bio-One, Frickenhausen, Germany), and the kinase reaction was initiated by addition of 2 µl of the solution containing peptide substrate and ATP. After 60 min incubation at 32° C., the reaction was stopped by addition of 20 µl of a solution containing 100 mM Hepes-NaOH, pH 7.4, 0.015% (v/v) Brij-35, 45 mM EDTA and 0.227% chip coating reagent 1 (Caliper Lifescience Inc, Hopkinton, Mass.). Phosphorylation of the substrate peptide was then detected on a Caliper 3000 instrument essentially as described by Pommereau et al (J. Biomol. Screening 9(5), 409-416, 2004). Separation conditions were as follows: Pressure –1.3 psi, upstream voltage –1562 V, downstream voltage –500 V, sample sip time 200 ms. Positive controls (buffer 1 instead of compound) and negative controls (buffer 1 instead of compound and buffer 2 instead of ROCK II) were run in parallel on each plate.

The following products/compounds were tested in said assay by using the respective form (salt or free base) obtained as in the examples described above and the following activities were measured.

| Compound No. | pIC50 |
|---|---|
| 21 | ++++ |
| 22 | +++++ |
| 27 | ++++ |
| 31 | +++++ |
| 41 | ++++ |
| 45 | +++++ |
| 48 | +++++ |
| 49 | ++++ |
| 50 | +++++ |
| 69 | ++++ |
| 75 | +++++ |
| 76 | +++++ |

The given activity is denoted as the negative decadal logarithm of the IC$_{50}$ (pIC$_{50}$) as follows:

| | |
|---|---|
| +: | pIC50 ≤ 3.0 |
| ++: | 3.0 ≤ pIC$_{50}$ < 4.0 |
| +++ | 4.0 ≤ pIC$_{50}$ < 5.0 |
| ++++: | 5.0 ≤ pIC$_{50}$ < 6.0 |
| +++++: | 6.0 ≤ pIC$_{50}$ |

The invention claimed is:
1. A compound of the formula (I)

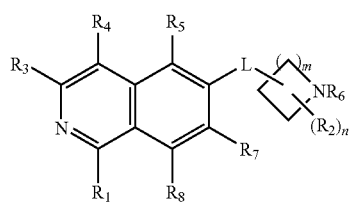

wherein
$R_1$ is H, OH or NH$_2$
$R_2$ is
(C$_6$-C$_{10}$)aryl,
(C$_7$-C$_8$)alkyl,
(C$_2$-C$_6$)alkenyl,
(C$_2$-C$_6$)alkynyl,
(C$_1$-C$_6$)alkylene-C(O)NH$_2$,
(C$_1$-C$_6$)alkylene-C(O)NH—(C$_1$-C$_6$)alkyl,
(C$_1$-C$_6$)alkylene-C(O)N[(C$_1$-C$_6$)alkyl]$_2$,
(C$_1$-C$_6$)alkylene-C(O)O—(C$_1$-C$_6$)alkyl,
C(O)O—(C$_1$-C$_6$)alkyl,
C(O)(C$_1$-C$_6$)alkyl,
C(O)NH—(C$_1$-C$_6$)alkyl,
C(O)NHR',
C(O)—NH(C$_2$-C$_6$)alkenyl,
C(O)—NH(C$_2$-C$_6$)alkynyl,
C(O)—NH(C$_1$-C$_6$)alkylene-R',
C(O)N[(C$_1$-C$_6$)alkyl]$_2$ or
$R_2$ is (C$_1$-C$_6$)alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$; or
$R_2$ is a (C$_1$-C$_4$)alkylene bound to the cyclic amine, in which the (C$_1$-C$_4$) alkylene forms a second bond to a different carbon atom of the cyclic amine ring and forms, together with carbon atoms of cyclic amine, a second, 4-8 membered ring;
$R_3$ is
H,
halogen,
(C$_1$-C$_6$)alkyl,
(C$_1$-C$_6$)alkylene-R',
OH,
O—R",
NH$_2$,
NHR",
NR"R" or
NH—C(O)—R",
$R_4$ is
H,
halogen,
hydroxy,
CN,
(C$_1$-C$_6$)alkyl;
$R_5$ is
H,
halogen,
CN,
NO$_2$,
(C$_1$-C$_6$)alkyl,
(C$_2$-C$_6$)alkenyl,
CH(OH)—(C$_1$-C$_6$)alkyl,
NH$_2$,
NH—SO$_2$H,
NH—SO$_2$—(C$_1$-C$_6$)alkyl,
NH—C(O)—(C$_1$-C$_6$)alkyl,
C(O)N[(C$_1$-C$_6$)alkyl]$_2$,
C(O)OH, or
C(O)O—(C$_1$-C$_6$)alkyl;
$R_6$ is
H,
R',
(C$_1$-C$_8$)alkyl,
(C$_1$-C$_6$)alkylene-R',
(C$_1$-C$_6$)alkylene-O—(C$_1$-C$_6$)alkyl,
(C$_1$-C$_6$)alkylene-O—R', ($C_1$-$C_6$)alkylene-CH[R']$_2$,
($C_1$-$C_6$)alkylene-C(O)—R',
($C_1$-$C_6$)alkylene-C(O)NH$_2$,
($C_1$-$C_6$)alkylene-C(O)NH—R',
($C_1$-$C_6$)alkylene-C(O)NH—($C_1$-$C_6$)alkyl,
($C_1$-$C_6$)alkylene-C(O)N[($C_1$-$C_6$)alkyl]$_2$,
($C_1$-$C_6$)alkylene-C(O)N[R']$_2$;
($C_1$-$C_6$)alkylene-C(O)O—($C_1$-$C_6$)alkyl,
C(O)O—($C_1$-$C_6$)alkyl,
C(O)OR',
C(O)($C_1$-$C_6$)alkyl,
C(O)R',
C(O)NH—($C_1$-$C_6$)alkyl,
C(O)NHR',
C(O)N[($C_1$-$C_6$)alkyl]R'
C(O)N[($C_1$-$C_6$)alkyl]$_2$,
C(O)—($C_1$-$C_6$)alkylene-R', or
C(O)O($C_1$-$C_6$)alkylene-R';
$R_7$ is
H,
halogen,
CN,
NO$_2$,
($C_1$-$C_6$)alkyl,
O—($C_1$-$C_6$)alkyl,
($C_2$-$C_6$)alkenyl,
CH(OH)—($C_1$-$C_6$)alkyl,
NH$_2$,
NH—SO$_2$H,
NH—SO$_2$—($C_1$-$C_6$)alkyl,
SO$_2$—NH$_2$,
NH—C(O)—($C_1$-$C_6$)alkyl,
C(O)N[($C_1$-$C_6$)alkyl]$_2$,
C(O)OH, or
C(O)O—($C_1$-$C_6$)alkyl;
$R_8$ is H, halogen or ($C_1$-$C_6$)alkyl;
n is 1;
m is 3;
L is O—(CH$_2$)p, S(CH$_2$)p, S(O)(CH$_2$)p, S(O)(CH$_2$)p, SO$_2$(CH$_2$)p, NH(CH$_2$)p, N($C_1$-$C_6$)alkyl-(CH$_2$)p, N($C_3$-$C_6$)cycloalkyl-(CH$_2$)p, N[CO($C_1$-$C_6$)alkyl]-(CH$_2$)p or N[($C_1$-$C_3$)alkylene-R']-(CH$_2$)p;
p is 0, 1, 2, 3, or 4;
R' is
($C_3$-$C_8$)cycloalkyl,
($C_5$-$C_{10}$)heterocyclyl,
($C_6$-$C_{10}$)aryl;
R" is
($C_3$-$C_8$)cycloalkyl,
($C_5$-$C_{10}$)heterocyclyl,
($C_6$-$C_{10}$)aryl,
($C_1$-$C_6$)alkyl,
($C_1$-$C_6$)alkylene-R',
($C_1$-$C_6$)alkylene-O—($C_1$-$C_6$)alkyl,
($C_1$-$C_6$)alkylene-O—R', or
($C_1$-$C_6$)alkylene-NR$_x$R$_y$; and
R$_x$ and R$_y$ are independently of each other
($C_1$-$C_6$)alkyl,
($C_5$-$C_{10}$)heterocyclyl,
($C_6$-$C_{10}$)aryl,
($C_1$-$C_4$)alkylene-($C_5$-$C_{10}$)heterocyclyl,
($C_1$-$C_4$)alkylene-($C_6$-$C_{10}$)aryl,
($C_1$-$C_4$)alkylene-NH($C_1$-$C_6$)alkyl,
($C_1$-$C_4$)alkylene-N[($C_1$-$C_6$)alkyl]$_2$,
($C_1$-$C_4$)alkylene-N[($C_6$-$C_{10}$)aryl]$_2$, or
($C_1$-$C_4$)alkylene-N[($C_5$-$C_{10}$)heterocyclyl]$_2$;
wherein in residues $R_2$, $R_4$, $R_5$, $R_6$, $R_7$ and $R_8$ as alkyl, alkylene or cycloalkyl can optionally be substituted one or more times by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
wherein in residues $R_2$ to $R_8$ as alkyl or alkylene can optionally be substituted one or more times by halogen;
wherein in residues $R_2$, $R_3$, $R_6$ as ($C_6$-$C_{10}$)aryl and ($C_5$-$C_{10}$)heterocyclyl are unsubstituted or substituted one or more times by suitable groups independently selected from halogen, OH, NO$_2$, N$_3$, CN, C(O)—($C_1$-$C_6$)alkyl, COOH, COO($C_1$-$C_6$)alkyl, CONH$_2$, CONH($C_1$-$C_6$)alkyl, CON[($C_1$-$C_6$)alkyl]$_2$, ($C_1$-$C_6$)alkyl, ($C_1$-$C_6$)alkylene-OH, ($C_1$-$C_6$)alkylene-NH$_2$, ($C_1$-$C_6$)alkylene-NH($C_1$-$C_6$)alkyl, ($C_1$-$C_6$)alkylene-N[($C_1$-$C_6$)alkyl]$_2$, ($C_2$-$C_6$)alkenyl, ($C_2$-$C_6$)alkynyl, O—($C_1$-$C_6$)alkyl, O—C(O)—($C_1$-$C_6$)alkyl, PO$_3$H$_2$, SO$_3$H, SO$_2$—NH$_2$, SO$_2$NH($C_1$-$C_6$)alkyl, SO$_2$N[($C_1$-$C_6$)alkyl]$_2$, S—($C_1$-$C_6$)alkyl; SO—($C_1$-$C_6$)alkyl, SO$_2$—($C_1$-$C_6$)alkyl, SO$_2$—N=CH—N[($C_1$-$C_6$)alkyl]$_2$, C(NH)(NH$_2$), NH$_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$)alkyl, NH—SO$_2$—($C_1$-$C_6$)alkyl, N($C_1$-$C_6$)alkyl-C(O)—($C_1$-$C_6$)alkyl, N($C_1$-$C_6$)alkyl-C(O)O—($C_1$-$C_6$)alkyl, N($C_1$-$C_6$)alkyl-C(O)—NH—($C_1$-$C_6$)alkyl]; or
stereoisomeric form thereof and/or tautomeric form thereof and/or pharmaceutically acceptable salt thereof.

2. The compound according to claim 1, having the formula (II)

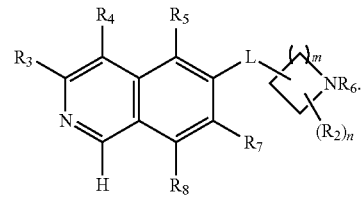

3. The compound according to claim 1, having the formula (III)

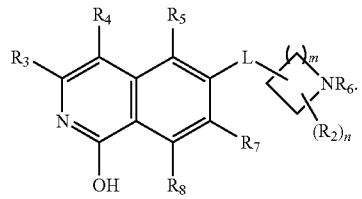

4. The compound according to claim 1, having the formula (III')

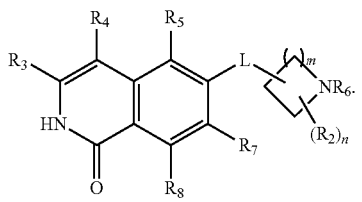

5. The compound according to claim 1 wherein $R_1$ is $NH_2$.

6. The compound according to claim 1, wherein $R_3$ is H, halogen, $(C_1-C_4)$alkylene-R', O—R" or NHR".

7. The compound according to claim 6, wherein $R_3$ is H or NHR".

8. The compound according to claim 7, wherein $R_3$ is H; NH—$(C_5-C_6)$heterocyclyl, or NH-phenyl.

9. The compound according to claim 8, wherein $R_3$ is H.

10. The compound according to claim 1, wherein $R_8$ is H, halogen or $(C_1-C_4)$alkyl.

11. The compound according to claim 10, wherein $R_8$ is H, Cl, F, methyl or ethyl.

12. The compound according to claim 11, wherein $R_8$ is H.

13. The compound according to claim 1, wherein $R_4$ is H, halogen or $(C_1-C_6)$alkyl.

14. The compound according to claim 13, wherein $R_4$ is H, halogen or $(C_1-C_4)$alkyl.

15. The compound according to claim 14, wherein $R_4$ is H.

16. The compound according to claim 1, wherein $R_5$ is H, halogen, CN, $(C_1-C_6)$alkyl, $(C_2-C_6)$alkenyl.

17. The compound according to claim 16, wherein $R_5$ is H, halogen, $(C_1-C_6)$alkyl, $(C_2-C_6)$alkenyl.

18. The compound according to claim 17, wherein $R_5$ is H, halogen, methyl, ethyl, vinyl.

19. The compound according to claim 18, wherein $R_5$ is H, halogen, methyl, or ethyl.

20. The compound according to claim 19, wherein $R_5$ is H.

21. The compound according to claim 1, wherein $R_7$ is H, halogen, CN, $(C_1-C_6)$alkyl, O—$(C_1-C_6)$alkyl, $(C_2-C_6)$alkenyl.

22. The compound according to claim 21, wherein $R_7$ is H, halogen, CN, $(C_1-C_4)$alkyl, O—$(C_1-C_4)$alkyl, $(C_2-C_4)$alkenyl.

23. The compound according to claim 22, wherein $R_7$ is H, fluoro, chloro, bromo, methyl, ethyl, methoxy, CN, or vinyl.

24. The compound according to claim 23, wherein $R_7$ is H, fluoro, chloro, bromo, methyl or methoxy.

25. The compound according to claim 24, wherein $R_7$ is H.

26. The compound according to claim 1, wherein $R_2$ is $(C_6-C_{10})$aryl, $(C_7-C_8)$alkyl, $(C_2-C_6)$alkenyl, $(C_1-C_6)$alkylene-C(O)NH$_2$, $(C_1-C_6)$alkylene-C(O)NH—$(C_1-C_6)$alkyl, $(C_1-C_6)$alkylene-C(O)N[$(C_1-C_6)$alkyl]$_2$, $(C_1-C_6)$alkylene-C(O)O—$(C_1-C_6)$alkyl, C(O)NH—$(C_1-C_6)$alkyl, C(O)NHR', C(O)—NH$(C_2-C_6)$alkenyl, C(O)—NH$(C_2-C_6)$alkynyl, C(O)—NH$(C_1-C_6)$alkylene-R', C(O)N[$(C_1-C_6)$alkyl]$_2$, or
  $R_2$ is $(C_1-C_6)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$; or
  $R_2$ is a $(C_1-C_4)$alkylene bound to the cyclic amine, in which the $(C_1-C_4)$ alkylene forms a second bond to a different carbon atom of the cyclic amine ring and forms, together with carbon atoms of cyclic amine, a second, 4-8 membered ring.

27. The compound according to claim 26, wherein $R_2$ is
$(C_6-C_{10})$aryl,
$(C_2-C_6)$alkenyl,
$(C_1-C_6)$alkylene-C(O)NH$_2$,
$(C_1-C_6)$alkylene-C(O)NH—$(C_1-C_6)$alkyl,
C(O)NH—$(C_1-C_6)$alkyl,
C(O)NHR',
C(O)—NH$(C_2-C_6)$alkenyl,
C(O)—NH$(C_2-C_6)$alkynyl, or
C(O)—NH$(C_1-C_6)$alkylene-R', or
  $R_2$ is $(C_1-C_3)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$; or
  $R_2$ is a $(C_1-C_4)$alkylene bound to the cyclic amine, in which the $(C_1-C_4)$ alkylene forms a second bond to a different carbon atom of the cyclic amine ring and forms, together with carbon atoms of cyclic amine, a second, 4-8 membered ring.

28. The compound according to claim 27, wherein $R_2$ is
$(C_6-C_{10})$aryl,
$(C_2-C_6)$alkenyl,
$(C_1-C_6)$alkylene-C(O)NH—$(C_1-C_6)$alkyl,
C(O)NH—$(C_1-C_6)$alkyl,
C(O)NHR',
C(O)—NH$(C_2-C_6)$alkynyl, or
C(O)—NH$(C_1-C_6)$alkylene-R', or
  $R_2$ is a $(C_1-C_2)$alkylene bound to the cyclic amine, in which the $(C_1-C_4)$ alkylene forms a second bond to a different carbon atom of the cyclic amine ring and forms, together with carbon atoms of cyclic amine, a second, 4-8 membered ring.

29. The compound according to claim 1, wherein
$R_6$ is
H,
$(C_1-C_6)$alkyl,
R',
$(C_1-C_4)$alkylene-$(C_6-C_{10})$aryl,
$(C_1-C_4)$alkylene-$(C_3-C_8)$cycloalkyl,
$(C_1-C_4)$alkylene-$(C_5-C_{10})$heterocyclyl,
$(C_1-C_6)$alkylene-O—$(C_1-C_6)$alkyl,
$(C_1-C_4)$alkylene-C(O)—$(C_5-C_{10})$heterocyclyl,
$(C_1-C_4)$alkylene-C(O)—$(C_6-C_{10})$aryl,
$(C_1-C_6)$alkylene-C(O)N[$(C_1-C_6)$alkyl]$_2$,
$(C_1-C_6)$alkylene-C(O)NH—$(C_1-C_6)$alkyl,
$(C_1-C_6)$alkylene-C(O)O—$(C_1-C_6)$alkyl,
C(O)O—$(C_1-C_6)$alkyl,
C(O)$(C_1-C_6)$alkyl,
C(O)R',
C(O)NH—$(C_1-C_6)$alkyl,
C(O)N[$(C_1-C_6)$alkyl]$_2$, or
C(O)$(C_1-C_6)$alkylene-R'.

30. The compound according to claim 29, wherein $R_6$ is
H,
$(C_1-C_6)$alkyl,
$(C_5-C_{10})$heterocyclyl,
$(C_3-C_8)$cycloalkyl,
$(C_6-C_{10})$aryl,
$(C_1-C_4)$alkylene-$(C_3-C_8)$cycloalkyl,
$(C_1-C_4)$alkylene-$(C_5-C_{10})$heterocyclyl,
$(C_1-C_4)$alkylene-$(C_6-C_{10})$aryl,
$(C_1-C_6)$alkylene-O—$(C_1-C_6)$alkyl,
$(C_1-C_6)$alkylene-C(O)N[$(C_1-C_6)$alkyl]$_2$,
$(C_1-C_6)$alkylene-C(O)NH—$(C_1-C_6)$alkyl,
$(C_1-C_6)$alkylene-C(O)O—$(C_1-C_6)$alkyl,
C(O)O—$(C_1-C_6)$alkyl,
C(O)$(C_1-C_6)$alkyl,
C(O)$(C_5-C_{10})$heterocyclyl,
C(O)$(C_3-C_8)$cycloalkyl
C(O)NH—$(C_1-C_6)$alkyl,
C(O)N[$(C_1-C_6)$alkyl]$_2$,
C(O)$(C_1-C_6)$alkylene-$(C_3-C_8)$cycloalkyl,
C(O)$(C_1-C_6)$alkylene-$C_5-C_{10}$)heterocyclyl, or
C(O)$(C_1-C_6)$alkylene-$(C_6-C_{10})$aryl.

31. The compound according to claim 30, wherein
$R_6$ is
H,
$(C_1-C_6)$alkyl,
$(C_3-C_8)$cycloalkyl,
$(C_5-C_{10})$heterocyclyl,
$(C_6-C_{10})$aryl,
$(C_1-C_4)$alkylene-$(C_3-C_8)$cycloalkyl,
$(C_1-C_4)$alkylene-$(C_5-C_{10})$heterocyclyl,
$(C_1-C_4)$alkylene-$(C_6-C_{10})$aryl,
$(C_1-C_6)$alkylene-O—$(C_1-C_6)$alkyl,
$(C_1-C_6)$alkylene-C(O)NH—$(C_1-C_6)$alkyl,
$(C_1-C_6)$alkylene-C(O)N[$(C_1-C_6)$alkyl]$_2$,
C(O)O—$(C_1-C_6)$alkyl,
C(O)$(C_1-C_6)$alkyl,
C(O)$(C_3-C_8)$cycloalkyl,
C(O)—$(C_5-C_{10})$heterocyclyl,
C(O)NH—$(C_1-C_6)$alkyl,
C(O)N[$(C_1-C_6)$alkyl]$_2$,
C(O)$(C_1-C_6)$alkylene-$(C_3-C_8)$cycloalkyl,
C(O)$(C_1-C_6)$alkylene-$(C_5-C_{10})$heterocyclyl, or
C(O)$(C_1-C_6)$alkylene-$(C_6-C_{10})$aryl.

32. The compound according to claim 31, wherein
$R_6$ is
H,
$(C_1-C_6)$alkyl,
$(C_3-C_8)$cycloalkyl,
$(C_6-C_{10})$aryl,
$(C_1-C_4)$alkylene-$(C_3-C_8)$cycloalkyl,
$(C_1-C_4)$alkylene-$(C_5-C_{10})$heterocyclyl,
$(C_1-C_4)$alkylene-$(C_6-C_{10})$aryl,
$(C_1-C_4)$alkylene-O—$(C_1-C_4)$alkyl,
C(O)$(C_1-C_6)$alkyl,
C(O)$(C_3-C_8)$cycloalkyl,
C(O)—$(C_5-C_{10})$heterocyclyl,
C(O)$(C_1-C_4)$alkylene-$(C_5-C_{10})$heterocyclyl, or
C(O)$(C_1-C_4)$alkylene-$(C_6-C_{10})$aryl.

33. The compound according to claim 32, wherein
$R_6$ is
H;
$(C_1-C_6)$alkyl;
$(C_3-C_8)$cycloalkyl;
$(C_1-C_4)$alkylene-$(C_3-C_8)$cycloalkyl;
$(C_1-C_4)$alkylene-$(C_5-C_{10})$heterocyclyl wherein heterocyclyl is unsubstituted or substituted one or more times by $(C_1-C_4)$alkyl;
$(C_1-C_4)$alkylene-$(C_6-C_{10})$aryl wherein aryl is unsubstituted or substituted one or more times by halogen, $(C_1-C_4)$alkyl, O—$(C_1-C_4)$alkyl, SO$_2$—$(C_1-C_4)$alkyl or SO$_2$-N[$(C_1-C_6)$alkyl]$_2$.

34. The compound according to claim 33, wherein $R_6$ is H, $(C_1-C_6)$alkyl or $(C_3-C_8)$cycloalkyl.

35. The compound according to claim 34, wherein $R_6$ is H, unsubstituted $(C_1-C_6)$alkyl or unsubstituted $(C_3-C_8)$cycloalkyl.

36. The compound according to claim 35, wherein $R_6$ is H.

37. The compound according to claim 1, wherein m is 3 and L is attached to the 3-position or to the 4-position of the piperidine ring.

38. The compound according to claim 1, wherein m is 3 and L is attached to the 4-position of the piperidine ring.

39. The compound according to claim 1, wherein L is S(CH$_2$)p, S(O)(CH$_2$)p or SO$_2$(CH$_2$)p.

40. The compound according to claim 1, wherein L is NH(CH$_2$)p or N$(C_1-C_6)$alkyl-(CH$_2$)p.

41. The compound according to claim 1, wherein L is O—(CH$_2$)p.

42. The compound according to claim 1, wherein p is 0.

43. The compound according to claim 1, wherein
$R_1$ is H or OH;
$R_2$ is $(C_6-C_{10})$aryl, $(C_7-C_8)$alkyl, $(C_2-C_6)$alkenyl, $(C_1-C_6)$alkylene-C(O)NH$_2$, $(C_1-C_6)$alkylene-C(O)NH—$(C_1-C_6)$alkyl, $(C_1-C_6)$alkylene-C(O)N[$(C_1-C_6)$alkyl]$_2$, $(C_1-C_6)$alkylene-C(O)O—$(C_1-C_6)$alkyl, C(O)NH—$(C_1-C_6)$alkyl, C(O)NHR', C(O)—NH$(C_2-C_6)$alkenyl, C(O)—NH$(C_2-C_6)$alkynyl, C(O)—NH$(C_1-C_6)$alkylene-R', C(O)N[$(C_1-C_6)$alkyl]$_2$, or
$R_2$ is $(C_1-C_6)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$; or
$R_2$ is a $(C_1-C_4)$alkylene bound to the cyclic amine, in which the $(C_1-C_4)$ alkylene forms a second bond to a different carbon atom of the cyclic amine ring and forms, together with carbon atoms of cyclic amine, a second, 4-8 membered ring;
$R_3$ is H, halogen, $(C_1-C_4)$alkylene-R', O—R" or NHR";
$R_4$ is H, halogen or $(C_1-C_6)$alkyl;
$R_5$ is H, $(C_1-C_6)$alkyl, halogen, CN, $(C_2-C_6)$alkenyl;
$R_6$ is H, R', $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)NH$_2$, $(C_1-C_6)$alkylene-C(O)NH—R', $(C_1-C_6)$alkylene-C(O)N[$(C_1-C_4)$alkyl]$_2$, $(C_1-C_6)$alkylene-C(O)N[R']$_2$; C(O)O—$(C_1-C_6)$alkyl, C(O)$(C_1-C_6)$alkyl, C(O)$(C_3-C_8)$cycloalkyl, C(O)NH—$(C_1-C_6)$alkyl, C(O)N[$(C_1-C_6)$alkyl]$_2$, C(O)$(C_1-C_6)$alkylene-$(C_3-C_8)$cycloalkyl, C(O)$(C_1-C_6)$alkylene-$C_5-C_{10})$heterocyclyl, or C(O)$(C_1-C_6)$alkylene-$(C_6-C_{10})$aryl; $R_7$ is H, halogen, CN, $(C_1-C_6)$alkyl, O—$(C_1-C_6)$alkyl, $(C_2-C_6)$alkenyl;
m is 3
n is 1,
L is O—(CH$_2$)p, S(CH$_2$)p, NH(CH$_2$)p or N$(C_1-C_6)$alkyl-(CH$_2$)p, and
p is 0, 1 or 2.

44. The compound according to claim 1, wherein
$R_1$ is H or OH;
$R_2$ is $(C_6-C_{10})$aryl, $(C_2-C_6)$alkenyl, $(C_1-C_6)$alkylene-C(O)NH$_2$, C(O)—NH$(C_2-C_6)$alkynyl, $(C_1-C_6)$alkylene-C(O)NH—$(C_1-C_6)$alkyl, C(O)NH—$(C_1-C_6)$alkyl, C(O)NHR' or C(O)—NH$(C_1-C_6)$alkylene-R', or
$R_2$ is $(C_1-C_3)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$; or
$R_2$ is a $(C_1-C_4)$alkylene bound to the cyclic amine, in which the $(C_1-C_4)$ alkylene forms a second bond to a different carbon atom of the cyclic amine ring and forms, together with carbon atoms of cyclic amine, a second, 4-8 membered ring;
$R_3$ is H, halogen or NHR";
$R_4$ is H, halogen or $(C_1-C_4)$alkyl;
$R_5$ is H, $(C_1-C_6)$alkyl, halogen, $(C_2-C_4)$alkenyl;
$R_6$ is H, $(C_3-C_8)$cycloalkyl, $(C_1-C_8)$alkyl, $(C_1-C_3)$alkylene-R', C(O)O—$(C_1-C_6)$alkyl, C(O)$(C_1-C_6)$alkyl, C(O)$(C_3-C_8)$cycloalkyl, C(O)—$(C_5-C_{10})$heterocyclyl, C(O)NH—$(C_1-C_6)$alkyl, C(O)N[$(C_1-C_6)$alkyl]$_2$, C(O)$(C_1-C_6)$alkylene-$(C_3-C_8)$cycloalkyl, C(O)$(C_1-C_6)$alkylene-$(C_5-C_{10})$heterocyclyl, or C(O)$(C_1-C_6)$alkylene-$(C_6-C_{10})$aryl;
$R_7$ is H, halogen, CN, $(C_1-C_6)$alkyl, O—$(C_1-C_6)$alkyl, $(C_2-C_6)$alkenyl;

m is 3
n is 1;
L is O—(CH$_2$)p, S(CH$_2$)p or NH(CH$_2$)p, and
p is 0 or 1.

45. The compound according to claim 1, wherein
R$_1$ is H or OH;
R$_2$ is
(C$_6$-C$_{10}$)aryl,
(C$_2$-C$_6$)alkenyl,
(C$_1$-C$_6$)alkylene-C(O)NH—(C$_1$-C$_6$)alkyl,
C(O)NH—(C$_1$-C$_6$)alkyl,
C(O)NHR',
C(O)—NH(C$_2$-C$_6$)alkynyl or
C(O)—NH(C$_1$-C$_6$)alkylene-R', or
R$_2$ is a (C$_1$-C$_2$)alkylene bound to the cyclic amine, in which the (C$_1$-C$_4$) alkylene forms a second bond to a different carbon atom of the cyclic amine ring and forms, together with carbon atoms of cyclic amine, a second, 4-8 membered ring;
R$_3$ is H, NH—(C$_5$-C$_6$)heteroaryl or NH-phenyl;
R$_4$ is H, halogen or (C$_1$-C$_4$)alkyl;
R$_5$ is H, (C$_1$-C$_4$)alkyl, halogen, (C$_2$-C$_4$)alkenyl;
R$_6$ is H, (C$_3$-C$_8$)cycloalkyl, (C$_1$-C$_8$)alkyl, (C$_1$-C$_3$)alkylene-R'; C(O)(C$_1$-C$_6$)alkyl, C(O)(C$_3$-C$_8$)cycloalkyl, C(O)—(C$_5$-C$_{10}$)heterocyclyl, C(O)(C$_1$-C$_3$)alkylene-(C$_5$-C$_{10}$)heterocyclyl or C(O)(C$_1$-C$_3$)alkylene-(C$_6$-C$_{10}$)aryl;
R$_7$ is H, halogen, CN, (C$_1$-C$_4$)alkyl, O—(C$_1$-C$_4$)alkyl, (C$_2$-C$_4$)alkenyl;
R$_8$ is H, halogen or (C$_1$-C$_4$)alkyl;
m is 3;
n is 1; and
L is O, NH or S.

46. A compound selected from the group consisting of
(2R,4R)-4-(Isoquinolin-6-yloxy)-piperidine-1,2-dicarboxylic acid 1-tert-butyl ester 2-methyl ester,
(2R,4R)-4-(Isoquinolin-6-yloxy)-2-o-tolylcarbamoyl-piperidine-1-carboxylic acid tert-butyl ester,
(2R,4R)-4-(Isoquinolin-6-yloxy)-piperidine-2-carboxylic acid o-tolylamide,
(2R,4R)-4-(Isoquinolin-6-yloxy)-piperidine-2-carboxylic acid isobutyl-amide,
(2R,4R)-4-(Isoquinolin-6-yloxy)-piperidine-2-carboxylic acid 3-methoxy-benzylamide (11),
(2R,4R)-4-(Isoquinolin-6-yloxy)-piperidine-2-carboxylic acid 2-chloro-benzylamide (12),
(2R,4R)-4-(Isoquinolin-6-yloxy)-piperidine-2-carboxylic acid phenethyl-amide,
(2R,4R)-4-(Isoquinolin-6-yloxy)-piperidine-2-carboxylic acid (3-methoxy-propyl)-amide,
(2R,4R)-4-(Isoquinolin-6-yloxy)-piperidine-2-carboxylic acid (2-hydroxy-ethyl)-amide,
(2R,4R)-4-(Isoquinolin-6-yloxy)-piperidine-2-carboxylic acid (furan-2-ylmethyl)-amide,
(2S,4S)-4-(Isoquinolin-6-yloxy)-piperidine-2-carboxylic acid (furan-2-ylmethyl)-amide,
(2S,4S)-4-(Isoquinolin-6-yloxy)-piperidine-2-carboxylic acid (3-methoxy-propyl)-amide,
(2S,4S)-4-(Isoquinolin-6-yloxy)-piperidine-2-carboxylic acid (pyridin-2-ylmethyl)-amide,
(2S,4S)-4-(Isoquinolin-6-yloxy)-piperidine-2-carboxylic acid prop-2-ynylamide,
(2S,4S)-4-(Isoquinolin-6-yloxy)-piperidine-2-carboxylic acid phenethyl-amide,
(2S,4S)-4-(Isoquinolin-6-yloxy)-piperidine-2-carboxylic acid 2-chloro-benzylamide,
(2S,4S)-4-(Isoquinolin-6-yloxy)-piperidine-2-carboxylic acid isobutyl-amide,
6-(8-Methyl-8-aza-bicyclo[3.2.1]oct-3-yloxy)-isoquinoline, and
6-(1-benzyl-4-phenyl-piperidin-4-yloxy)-7-chloro-isoquinolin-1-one, or
stereoisomeric form thereof and/or tautomeric form thereof and/or pharmaceutically acceptable salt thereof.

47. A compound selected from the group consisting of
6-(8-Methyl-8-aza-bicyclo[3.2.1]oct-3-yloxy)-2H-isoquinolin-1-one,
6-(8-Aza-bicyclo[3.2.1]oct-3-yloxy)-7-chloro-2H-isoquinolin-1-one,
6-(8-Methyl-8-aza-bicyclo[3.2.1]oct-3-yloxy)-2H-isoquinolin-1-one,
7-Chloro-6-(8-methyl-8-aza-bicyclo[3.2.1]oct-3-yloxy)-2H-isoquinolin-1-one,
7-Methyl-6-(8-methyl-8-aza-bicyclo[3.2.1]oct-3-yloxy)-2H-isoquinolin-1-one, and
N6-(4-Amino-4-phenyl-cyclohexyl)-isoquinoline-1,6-diamine, or
stereoisomeric form thereof and/or tautomeric form thereof and/or pharmaceutically acceptable salt thereof.

48. A pharmaceutical composition comprising a pharmaceutically effective amount of at least one compound according to claim 1 and/or a pharmacologically acceptable salt thereof, and physiologically tolerated excipient or carriers, and optionally one or more additives and/or one or more other active ingredients.

* * * * *